United States Patent [19]

Suzuki et al.

[11] Patent Number: 5,486,472
[45] Date of Patent: Jan. 23, 1996

[54] MONOCLONAL ANTIBODIES TO PACAP

[75] Inventors: Nobuhiro Suzuki, Ibaraki; Chieko Kitada, Osaka; Masao Tsuda, Ibaraki, all of Japan

[73] Assignee: Takeda Chemical Industries, Ltd., Osaka, Japan

[21] Appl. No.: 924,054

[22] PCT Filed: Mar. 15, 1991

[86] PCT No.: PCT/JP91/00354

§ 371 Date: Sep. 3, 1992

§ 102(e) Date: Sep. 3, 1992

[87] PCT Pub. No.: WO91/14786

PCT Pub. Date: Oct. 3, 1991

[30] Foreign Application Priority Data

Mar. 17, 1990 [JP] Japan .................................. 2-5565
Oct. 26, 1990 [JP] Japan .................................. 2-287115

[51] Int. Cl.$^6$ ........................... C12N 5/12; C07K 16/18; G01N 33/53
[52] U.S. Cl. ................. 435/240.27; 530/388.24; 530/388.1; 530/389.3; 530/389.1; 435/7.2; 435/7.93
[58] Field of Search ............ 530/388.24, 388.22, 530/387.9, 387.1, 389.1, 388.1, 389.3; 435/7.1, 7.93, 7.94, 7.92, 240.27

[56] References Cited

FOREIGN PATENT DOCUMENTS

0404034A2  12/1990  European Pat. Off. .

OTHER PUBLICATIONS

Maurer, P. H. et al, Methods in Enzymology, 70:49–70, 1980.
Sevier, E. D., et al., Clin Chem., 27(11):1797–1806, 1981.
Dialog Information Service, File 154: Medline, accession No. 07391864.
Chemical Abstracts. vol. 99, 128, 11656lg, 1983.
Chemical Abstracts, vol. 86, 412, 187443, 1977.
Recueil, Journal of the Royal Netherlands Chemical Society, vol. 101, 393–396, 1982.
British Medical Bulletin, vol. 30, No. 1, 1974.
Elsevier Science Publishers B. V. 129–138, 1984.
Biochemical and Biophysical Research Communications vol. 164, No. 1, 567–574, 1989.
Biochemical and Biophysical Research Communications vol. 166, No. 1 81–89, 1990.

*Primary Examiner*—Margaret Parr
*Assistant Examiner*—Susan A. Loring
*Attorney, Agent, or Firm*—David G. Conlin; David S. Resnick

[57] ABSTRACT

Disclosed are a monoclonal antibody having affinity for PACAP, a partial peptide thereof, a precursor thereof or VIP; a hybridoma cell which produces the above monoclonal antibody; and an immunoassay for assaying PACAP by a competitive method or a sandwich method using the above antibody, whereby PACAP can be specifically detected with high sensitivity.

11 Claims, 15 Drawing Sheets

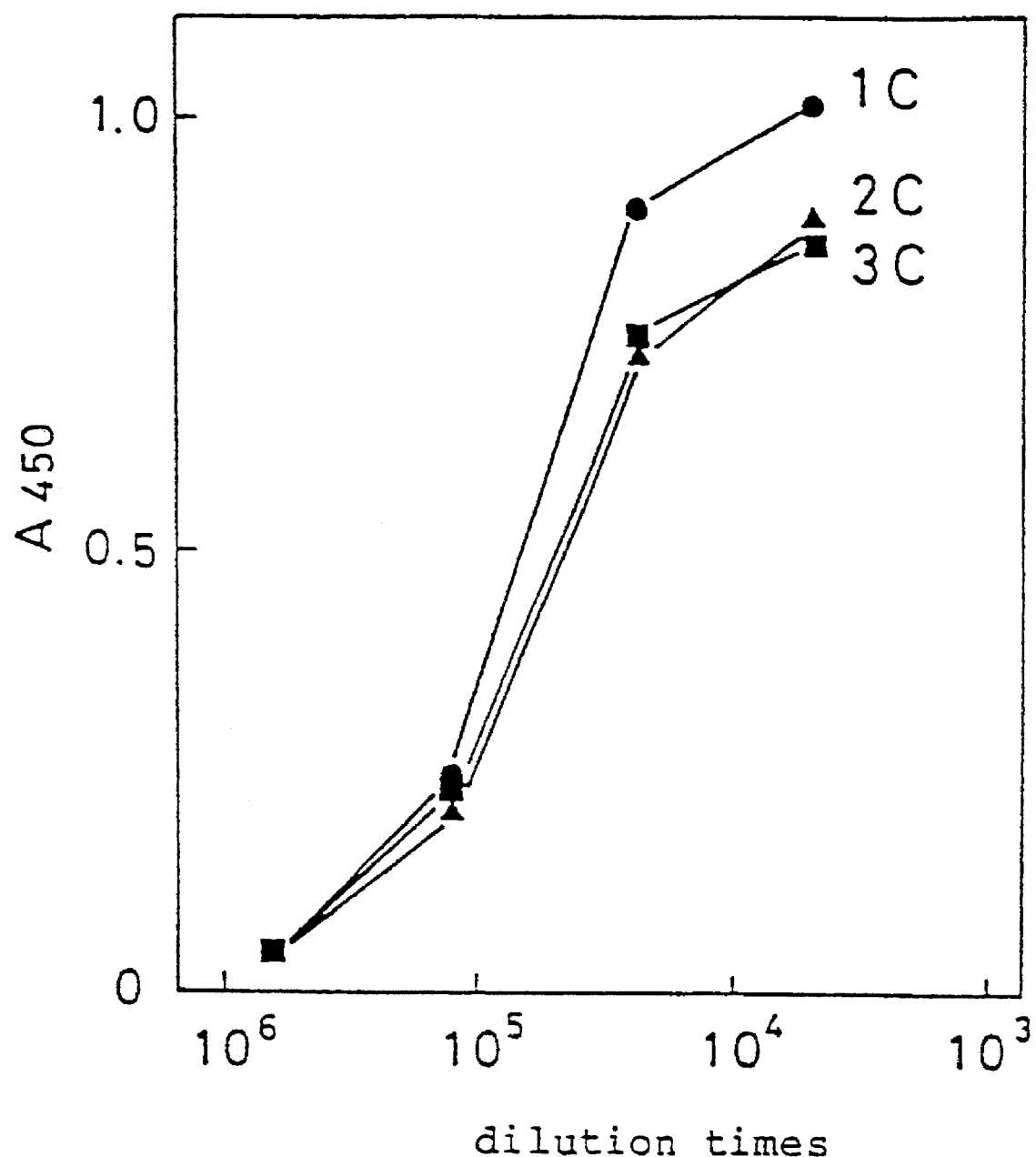
F I G. 2

(e) PA-2Ca(classIII)

(f) PA-1Ca(class IV)

MONOCLONAL ANTIBODIES TO PACAP

BACKGROUND OF THE INVENTION

The present invention relates to an antibody which is novel and useful in that it has specific affinity for PACAP, and more particularly to an antibody useful for development of assays of PACAP on the basis of antigen-antibody reactions or for diagnosis and treatment of diseases related to PACAP.

Various hormones secreted by brain hypothalami and hypophyses have been known. Examples thereof include thyrotropin releasing hormone, luteinizing hormone releasing hormone, somatostatin, adrenocorticotropic hormone, growth hormone and prolactin. Action thereof has been studied in detail. Recently, a novel bioactive substance of hypothalamic origin other than these hormones was studied based upon adenylate cyclase activity, and consequently a peptide consisting of 38 amino acid residues which had not been reported till then was discovered from sheep hypothalami. This peptide was named "PACAP38NH$_2$" and has a structure represented by the following formula (SEQ ID NO:2):

His Ser Asp Gly Ile Phe Thr Asp Ser Tyr Ser Arg Tyr Arg Lys
Gln Met Ala Val Lys Lys Tyr Leu Ala Ala Val Leu Gly Lys
Arg Tyr Lys Gln Arg Val Lys Asn Lys-NH$_2$

It was disclosed in applications for patents (Japanese Patent Application Nos. 1-155791/1990 and 1-284771/1990) on cDNA of sheep PACAP38, and an application for a patent (Japanese Patent Application No. 1-259924/1990) on the partial structure of cDNA of human PACAP38 that the amino acid sequence of the mature portion of sheep PACAP38 was the same as that of human PACAP38, and that some amino acids of the precursors thereof were substituted. It is deduced from the position of continuous basic amino acids shown in the cDNA sequence of PACAP38NH$_2$ that PACAP27NH$_2$, in addition to PACAP38NH$_2$, will exist as a peptide cut out of the precursor.

In fact, according to subsequent studies PACAP27NH$_2$ was also isolated from sheep hypothalami, in addition to PACAP38NH$_2$. The structure thereof is represented by the following formula (SEQ ID NO:2):
PACAP27NH$_2$ His Ser Asp Gly Ile Phe Thr Asp Ser Tyr Ser Arg Tyr Arg Lys
Gln Met Ala Val Lys Lys Tyr Leu Ala Ala Val Leu-NH$_2$ PACAP38NH$_2$ and PACAP27NH$_2$ are hereinafter represented by the general term of "PACAP". The 28 amino acid residues on the N-terminal side of PACAP38NH$_2$ containing PACAP27NH$_2$ show 68% homology with vasoactive intestinal polypeptide (VIP) well known as a brain-gut peptide. However, it has been reported that the adenylate cyclase activating activity of PACAP exceeds at least 1,000 times that of VIP.

Thus, the action of PACAP is anticipated to be different from that of VIP, and a deep interest is taken in the physiological role thereof and the relation thereof to the pathology.

Although the interest in PACAP is increased as described above, basic physiological information such as existing sites other than hypothalami of PACAP and a plasma level thereof is scarcely obtained, and the relation thereof to the pathology is also unknown. This is mainly caused by that any monoclonal antibodies specifically recognizing PACAP have hitherto not been prepared and that any immunoassays for assaying PACAP specifically and highly sensitively have not been developed. These immunological procedures are considered to be one of the most effective means to study PACAP, particularly the metabolic pathways thereof, the secretory mechanism thereof, the receptor system thereof, the relation thereof to the pathology and the like collectively. The establishment of these procedures has therefore been earnestly desired in various fields.

Previously, competitive radioimmunoassays (RIA) generally using one kind of antibody and enzyme immunoassays (EIA) have been developed and employed to assay low molecular weight peptides such as PACAP. On the other hand, sandwich immunoassays using two kinds of antibodies have the advantages of (1) improving the specificity of assay systems because of the use of two kinds of antibodies and (2) being little affected by nonspecific interfering factors because of the use of the antibodies in large excess to substances to be assayed. Until now, however, it has been unknown at all whether or not the low molecular weight peptides having no disulfide linkage such as PACAP can be assayed with high sensitivity by the sandwich methods. Namely, in case of the low molecular weight peptides having no disulfide linkage such as PACAP, the possibility is conceivable that binding sites of two kinds of antibodies are in so close proximity to each other as to exert influences such as steric hindrance, which results in difficulty of the establishment of highly sensitive sandwich methods.

SUMMARY OF THE INVENTION

The present inventors prepared polyclonal and monoclonal antibodies having affinity for PACAP and having different reaction specificity for partial peptides of PACAP and VIP, and developed an immunoassay which can specifically detect PACAP with high sensitivity using the antibodies and which can fractionate and determine PACAP38NH$_2$ and PACAP27NH$_2$.

In accordance with the present invention, there are provided a monoclonal antibody having affinity for PACAP, a partial peptide of PACAP, a precursor of PACAP or VIP; a hybridoma cell which produces the above monoclonal antibody; and an immunoassay for assaying PACAP by a competitive method or a sandwich method using the above antibody.

BRIEF DESCRIPTION OF THE DRAWINGS

FIG. 2 is a graph showing antibody titer to PACAP(11–27)NH$_2$ in rabbit antisera;

FIG. 3(a) shows the results using antibody PA-1Na. FIG. 3(b) shows the results using antibody PA-3Na. FIG. 3(c) shows the results using antibody PA-5Na. FIG. 3(d) shows the results using antibody PA-6Na. FIG. 3(e) shows the results using antibody PA-2Ca. FIG. 3(f) shows the results using antibody PA-1Ca;

FIG. 4 shows the results using PA-6Na F(ab')$_2$-HRP. FIG. 5 shows the results using PA-1Ca F(ab')$_2$-HRP. FIG. 6 shows the results using PA-2Ca IgG-HRP.

FIG. 8 shows the results using PA-1Na. FIG. 9 shows the results using PA-3Na. FIG. 10 shows the results using PA-5Na. FIG. 11 shows the results using PA-6Na.

DESCRIPTION OF THE PREFERRED EMBODIMENTS

Figure 1:
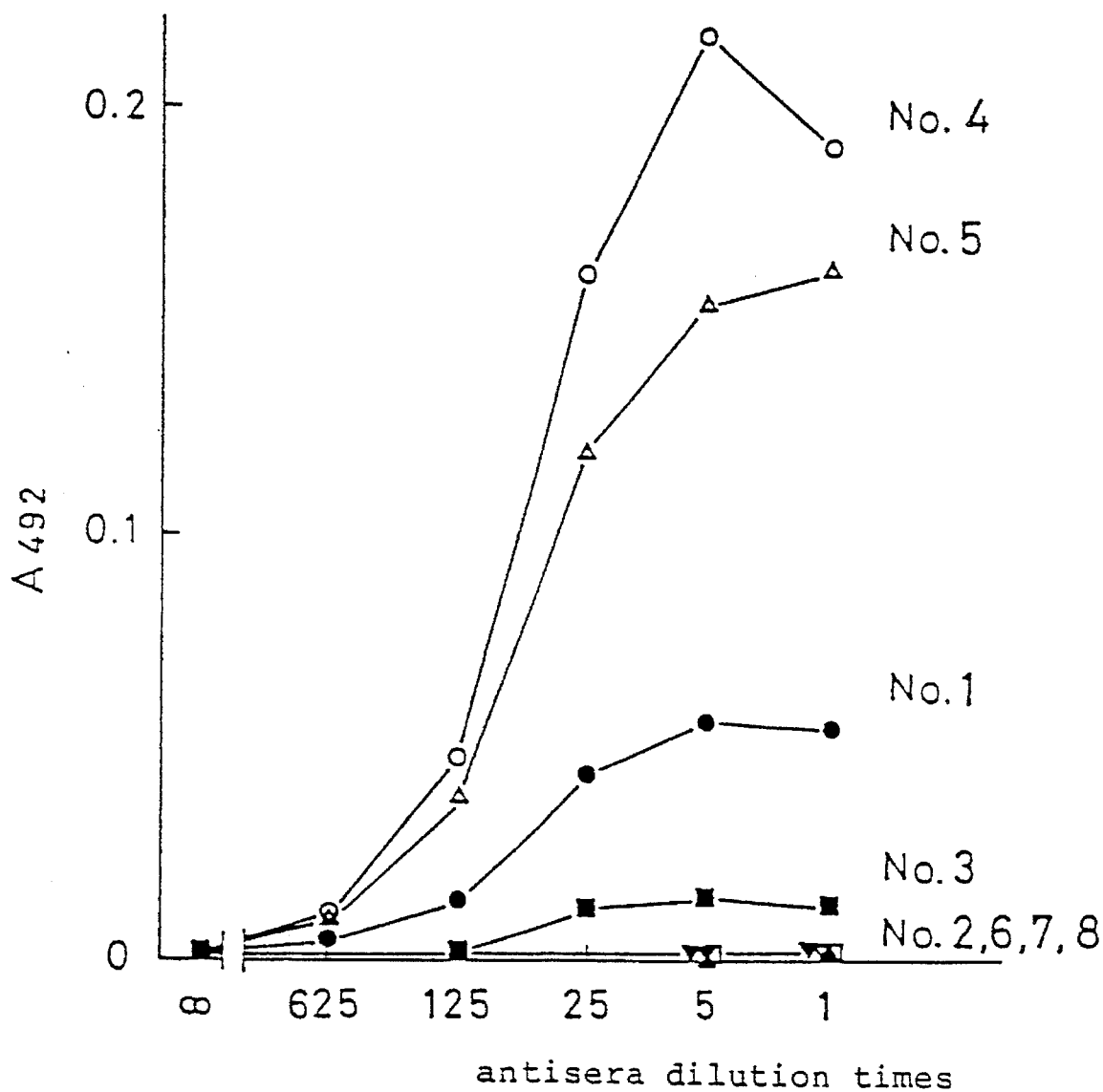
FIG. 1 is a graph showing antibody titer to PACAP38NH$_2$ in mouse antisera.

As the partial peptides of PACAP, any peptides may be used as long as they have partial sequences of PACAP. Examples of such peptides include peptides corresponding to an N-terminal portion of PACAP, such as PACAP(1–13) having the following sequence (SEQ ID NO:3):

His Ser Asp Gly Ile Phe Thr Asp Ser Tyr Ser Arg Tyr, peptides corresponding to a region from the N-terminal portion to a central portionb of PACAP, such as PACAP(4–27) having the following sequence (SEQ ID NO:4):

Gly Ile Phe Thr Asp Ser Tyr Ser Arg Tyr Arg Lys Gln Met
Ala Val Lys Lys Tyr Leu Ala Ala Val Leu, peptides corresponding to a region from a C-terminal portion to a central portion of PACAP38NH$_2$, such as PACAP(14–38) having the following sequence (SEQ ID NO:5):

Arg Lys Gln Met Ala Val Lys Lys Tyr Leu Ala Ala Val Leu
Gly Lys Arg Tyr Lys Gln Arg Val Lys Asn Lys, peptides corresponding to the C-terminal portion of PACAP38NH$_2$, such as PACAP(31–38) having the following sequence (SEQ ID NO:6):

Tyr Lys Gln Arg Val Lys Asn Lys, and peptides corresponding to a region from a central portion to a C-terminal portion of PACAP27, such as PACAP(11–27) having the following sequence (SEQ ID NO:7):

Ser Arg Tyr Arg Lys Gln Met Ala Val Lys Lys Tyr Leu Ala
Ala Val Leu—NH$_2$

Of these peptides, it is preferred that the C-termini of PACAP(31–38) and PACAP(11–27) have amide forms, and the C-termini of the other peptides may have either amide forms or free carboxylic acid forms. The amide form is represented by giving NH$_2$ as PACAP(31–38)NH$_2$, and the free carboxylic acid form is given no symbol or represented by giving OH, for example, PACAP(31–38)OH.

Examples of a precursor of PACAP include a precursor of human PACAP consisting of an amino acid sequence represented by the following formula (SEQ ID NO:8) or a portion thereof:

|     | Met | Thr | Met | Cys | Ser | Gly | Ala | Arg | Leu |
| --- | --- | --- | --- | --- | --- | --- | --- | --- | --- |
| Ala | Leu | Leu | Val | Tyr | Gly | Ile | Ile | Met | His |
| Ser | Ser | Val | Tyr | Ser | Ser | Pro | Ala | Ala | Ala |
| Gly | Leu | Arg | Phe | Pro | Gly | Ile | Arg | Pro | Glu |
| Glu | Glu | Ala | Tyr | Gly | Glu | Asp | Gly | Asn | Pro |
| Leu | Pro | Asp | Phe | Gly | Gly | Ser | Glu | Pro | Pro |
| Gly | Ala | Gly | Ser | Pro | Ala | Ser | Ala | Pro | Arg |
| Ala | Ala | Ala | Ala | Trp | Tyr | Arg | Pro | Ala | Gly |
| Arg | Arg | Asp | Val | Ala | His | Gly | Ile | Leu | Asn |
| Glu | Ala | Tyr | Arg | Lys | Val | Leu | Asp | Gln | Leu |
| Ser | Ala | Gly | Lys | His | Leu | Gln | Ser | Leu | Val |
| Ala | Arg | Gly | Val | Gly | Gly | Ser | Leu | Gly | Gly |
| Gly | Ala | Gly | Asp | Asp | Ala | Glu | Pro | Leu | Ser |
| Lys | Arg | His | Ser | Asp | Gly | Ile | Phe | Thr | Asp |
| Ser | Tyr | Ser | Arg | Tyr | Arg | Lys | Gln | Met | Ala |
| Val | Lys | Lys | Tyr | Leu | Ala | Ala | Val | Leu | Gly |
| Lys | Arg | Tyr | Lys | Gln | Arg | Val | Lys | Asn | Lys |
| Gly | Arg | Arg | Ile | Ala | Tyr | Leu |     |     |     |

The present inventors made various investigations to produce the monoclonal antibodies and the polyclonal antibodies to PACAP. As a result, the antibodies roughly classified into 5 classes were obtained.

The antibodies classified as class I recognize the N-terminal portion of PACAP. Namely, they react with PACAP38NH$_2$, PACAP27NH$_2$, PACAP(1–13) and PACAP(4–27), and do not react with PACAP(14–38)NH$_2$ and PACAP(31–38)NH$_2$.

The antibodies classified as class II recognize the region from the N-terminal portion to the central portion of PACAP. Namely, they react with PACAP38, PACAP27NH$_2$ and PACAP(4–27), and do not react with PACAP(1–13), PACAP(14–28)NH$_2$ and PACAP(31–38)NH$_2$.

The antibodies classified as class III recognize the region from the C-terminal portion to the central portion of PACAP. Namely, they react with PACAP38NH$_2$ and PACAP(14–38)NH$_2$, and do not react with PACAP27NH$_2$, PACAP(1–13), PACAP(4–27) and PACAP(31–38)NH$_2$.

The antibodies classified as class IV recognize the C-terminal portion of PACAP38NH$_2$. Namely, they react with PACAP38NH$_2$, PACAP(14–38)NH$_2$ and PACAP(31–38)NH$_2$, and do not react with PACAP27NH$_2$, PACAP(4–27) and PACAP(1–13).

The antibodies classified as class V recognize the C-terminal portion of PACAP27NH$_2$. Namely, they are antibodies to PACAP(11–27)NH$_2$.

The antibodies classified as class I are further classified into class Ia and class Ib. The antibodies classified as class Ia exhibit only a cross reactivity with VIP of less than 0.5%, and the antibodies classified as class Ib exhibit a cross reactivity with VIP of 0.5% or more.

Many of the antibodies classified as class II show only a cross reactivity with VIP of less than 0.5%, and many of the antibodies classified as classes III to V exhibit only a cross reactivity with VIP of less than 0.01%.

These antibodies can be used in ordinary tissue staining or competitive immunoassays. The present inventors further made various investigations to develop an excellent immunoassay, and consequently developed the sandwich immunoassay in which to kinds of these monoclonal or polyclonal antibodies are used in combination.

In the immunoassay for assaying PACAP by the sandwich method of the present invention, each of the antibodies used in a primary reaction (a reaction of an antibody for a solid phase with a substance to be tested) and a secondary reaction (a reaction of a labeled antibody with the substance to be tested) may be either the polyclonal antibody or the monoclonal antibody. It is however preferred that one of them is the antibody which recognizes the N-terminal portion of PACAP38NH$_2$ (class I), the region from the N-terminal portion to the central portion (class II), the region from the C-terminal portion to the central portion (class III) or C-terminal portion (class IV) and the other is the antibody which recognizes regions other than the regions described above.

Namely, the present inventors discovered that PACAP38NH$_2$ was detected with high sensitivity in combinations of class I and class III, class II and class IV, and class I and class IV, or in the sandwich method using the antibodies in combination which did not recognize the regions adjacent to each other. The present inventors further discovered that PACAP38NH$_2$ was also detected in combinations of class I and class II, class II and class III, and class III and class IV, or in the sandwich method using the antibodies in combination which recognize the regions adjacent to each other, and particularly that PACAP38NH$_2$ was detected with high sensitivity in the sandwich method in which the antibody of class II was used in combination with the antibody of class III. The sandwich immunoassay is specific for PACAP38NH$_2$. For example, in the sandwich immunoassay using PA-6Na, one of the antibodies belonging to class II, and PA-2Ca, one of the antibodies belonging to class III, it was discovered that the cross reactivity with other peptides having homology with VIP and PACAP38NH$_2$ was 0.001% or less. Examples of such peptides include growth hormone releasing hormone (GRF) having the following sequence (SEQ ID NO:9):

Tyr—Ala—Asp—Ala—Ile—Phe—Thr—Asn—Ser—Tyr—Arg—
Lys—Val—Leu—Gly—Gln—Leu—Ser—Ala—Arg—Lys—Leu—
Leu—Gln—Asp—Ile—Met—Ser—Arg—Gln—Gln—Gly—Glu—
Ser—Asn—Gln—Glu—Arg—Gly—Ala—Arg—Ala—Arg—Leu—NH$_2$, and secretin, a typical gastrointestinal hormone having the following sequence (SEQ ID NO:10)

His—Ser—Asp—Gly—Thr—Phe—Thr—Ser—Glu—Leu—Ser—
Arg—Leu—Arg—Glu—Gly—Ala—Arg—Leu—Gln—Arg—
Leu—Leu—Gln—Gly—Leu—Val—NH$_2$ (molecular weight: 3039.4)

In the immunoassay for assaying PACAP27NH$_2$ by the sandwich method of the present invention, each of the antibodies used in the primary and secondary reactions may be either the polyclonal antibody or the monoclonal antibody. It is however preferred that one of them is the antibody which recognizes the N-terminal portion of PACAP27NH$_2$ (class I), the region from the N-terminal portion to the central portion (class II) or C-terminal portion (class V) and the other is the antibody which recognizes regions other than the regions described above. Also in this sandwich immunoassay of the present invention, PACAP27NH$_2$ can be detected without cross reaction with VIP, GRF or secretin (the cross reactivity is 0.001% or less). The sandwich immunoassay using either the antibody of class I or that of class II in combination with either the antibody of class III or that of class IV is specific for PACAP38NH$_2$ and does not cross react with PACAP27NH$_2$. On the other hand, the immunoassay for assaying PACAP27NH$_2$ by the sandwich method using either the antibody of class I or that of class II in combination with the antibody of class V shows a cross reactivity with PACAP38NH$_2$ as low as 0.22 to 3.6% by weight ratio or 0.31 to 5% by molar ratio. By using these immunoassays, therefore, PACAP38NH$_2$ and PACAP27NH$_2$ can be fractionated and determined.

The polyclonal antibody used in the present invention is usually prepared by producing a complex comprising a carrier protein and PACAP or a partial peptide of PACAP, which acts as an immunogen. Next, animals are inoculated with this complex for immunization. The substance containing an anti-PACAP or anti-PACAP partial peptide antibody from the immunized animals is recovered, and the antibody is then separated and purified.

The monoclonal antibody of the present invention is prepared by selecting individuals having high antibody titer from the above-mentioned immunized animals, recovering spleens or lymphatic corpuscles therefrom 2 to 5 days after the final immunization, fusing antibody producing cells contained therein with myeloma cells, and selecting hybridoma cells which stably produce an antibody having high titer to obtain monoclonal hybridoma cells.

Both of natural purified samples and synthetic samples can be used as immunogens. PACAP and portions thereof are used. Compounds containing the structure of PACAP or portions of PACAP are used as the immunogens in some cases.

The various peptides used in the present invention can be prepared by peptide synthesis methods known to those skilled in the art. Either the solid phase synthesis methods or the liquid phase synthesis methods may be used. Examples of the peptide synthesis methods include methods described in B. Merrifield [*J. Am. Chem. Soc.* 85, 2149 (1963)], M. Bodanszky and M. A. Ondetti [*Peptide Synthesis*, Interscience Publishers, New York (1966)], Schroder and Lubke [*The Peptide*, Academic Press, New York (1965)], N. Izumiya et al. [*Fundamentals and Experiments of Peptide Synthesis*, Maruzen (1985)] and H. Yajima and S. Sakakibara [*Course of Biochemical Experiments* 1, *Chemistry of Proteins IV* 205 (1977)].

For example, when PACAP38NH$_2$ or a partial peptide of PACAP38NH$_2$ is synthesized by the solid phase methods, using any of the insoluble resins known in the art such as chloromethyl resins, 4-methylbenzhydrylamine resins and 4-oxymethylphenylacetamidomethyl resins, protected amino acids are successively condensed to the C-terminal side of PACAP38NH$_2$ or of the partial peptide of PACAP38NH$_2$ according to methods known in the art. Then, all protecting groups are removed by hydrogen fluoride treatment, followed by purification by methods known in the art such as high performance liquid chromatography, whereby the desired PACAP38NH$_2$ or partial peptide of PACAP38NH$_2$ can be obtained.

For example, the N-protected amino acids can be produced by protecting α-amino groups with Boc groups, the hydroxyl groups of serine and threonine with Bzl groups, the ω-carboxylic acid groups of glutamic acid and aspartic acid with OBzl groups, the -amino group of lysine with a Cl-Z group, the hydroxyl group of tyrosine with a Br-Z group, the guanido group of arginine with a Tos group, and the imidazole group of histidine with a Tos group.

The abbreviations used in this specification, are the abbreviations adopted by IUPAC-IUB Commission on Biochemical Nomenclature or commonly used in the art are employed. For example, the following abbreviations are used. When an optical isomer is capable of existing with respect to the amino acids, the L-form is represented unless otherwise specified.

PAM: Phenylacetamidomethyl
BHA: Benzhydrylamine
Boc: t-Butyloxycarbonyl

Cl-Z: 2-Chloro-benzyloxycarbonyl
Br-Z: 2-Bromo-benzyloxycarbonyl
Bzl: Benzyl
OBzl: Benzyl ester
Tos: p-Toluenesulfonyl
HOBt: 1-Benzotriazole
DCC: N,N'-Dichlorohexylcarbodiimide
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine With respect to the protein complexes comprising the immunogens and the carrier proteins used for immunization of mammals, any type of carrier proteins may be coupled with haptens in any ratio, as long as the antibodies can be produced effectively to the haptens coupled with the carrier proteins to be immunized. For example, bovine serum albumin, bovine thyroglobulin or hemocyanin is coupled with the hapten in a weight ratio of 0.1 to 20, and preferably 1 to 5, per 1 of the hapten.

Various condensing agents may be used for the coupling of the haptens and the carrier proteins. In particular, glutaraldehyde, carbodiimide active esters, maleimide active esters and active ester reagents containing thiol groups or dithiopyridyl groups are advantageously used.

The condensed products are given alone or with carriers or diluents to warm-blooded animals at sites where the antibodies are capable of being produced. In giving the condensed products, Freund's complete adjuvant or Freund's incomplete adjuvant may be given to enhance the antibody productivity. The condensed products are usually given once every 2 to 6 weeks, 3 to 6 times in all.

The warm-blooded animals used therein include, for example, monkeys, rabbits, dogs, guinea pigs, mice, rats, sheep, goats and chickens.

The antibodies are harvested from the blood, the ascites and the like (preferably from the blood) of the warm-blooded animals immunized by the methods described above. The titer of the anti-PACAP antibody in the antiserum is determined, for example, by reacting labeled PACAP described below with the antiserum, and then measuring the activity of a labeling agent bound to the antibody. The antibodies are separated and purified according to methods for separating and purifying immunoglobulin which are known in the art. Such methods include salt precipitation, alcohol precipitation, isoelectric precipitation, electrophoresis, adsorption and desorption using an ion exchanger (for example, DEAE), ultracentrifugation, gel filtration and specific purifying methods for obtaining antibodies by recovering the antibodies alone by using active adsorbents such as antigen-antibody complexes, protein A and protein G and then breaking the binding.

The antibodies thus obtained comprise mainly of IgG and also contain additional immunoglobulins such as IgM and IgA.

The anti-PACAP antibody producing hybridoma cells of the present invention can be prepared by selecting individuals having high antibody titer from the warm-blooded animals such as mice immunized similarly to the above method for preparing the polyclonal antibody, recovering spleens or lymphatic corpuscles therefrom 2 to 5 days after the final immunization, and fusing antibody producing cells contained therein with myeloma cells. The cells may be fused according to methods known in the art, for example, the method of Kohler and Milstein [Nature 256, 495 (1975)]. Fusion accelerators include polyethylene glycol (PEG) and Sendai virus. In particular, PEG is preferably used.

The myeloma cells include, for example, NS-1, P3U1 and SP2/0. In particular, P3U1 is preferably used. The ratio of the number of the antibody producing cells (splenic cells) to the myeloma cells is preferably about 1:1 to 20:1. PEG(preferably PEG 1,000 to PEG 6,000) is added in a concentration of about 10 to 80%, and incubated at 20° to 40° C., preferably 30° to 37° C. for 1 to 10 minutes, whereby the cell fusion can be effectively performed.

The anti-PACAP antibody producing hybridoma cells can be screened by various methods known in the art. Examples of such methods include an enzyme immunoassay (EIA) which comprises adding a hybridoma culture supernatant to a solid phase (for example, a microplate) allowed to adsorb PACAP or the partial peptide thereof, then adding an anti-immunoglobulin antibody (when mouse cells are used for the cell fusion, an anti-mouse immunoglobulin antibody is employed) labeled with horseradish peroxidase (HRP) or protein-A thereto, and detecting the anti-PACAP monoclonal antibody; and an enzyme immunoassay (EIA) which comprises adding a hybridoma culture supernatant to a solid phase allowed to adsorb an anti-immunoglobulin antibody or protein A, then adding HRP-labeled PACAP, and detecting the anti-PACAP monoclonal antibody bound to the solid phase. Selection and breeding of the anti-PACAP monoclonal antibodies are usually achieved by addition of HAT (hypoxanthine, aminopterin and thymidine) and by use of a medium for animal cells containing 10 to 20% fetal calf serum, such as RPMI 1640. The antibody titer of the hybridoma culture supernatant can be assayed similarly to the above-mentioned method for assaying the titer of the anti-PACAP antibody in antiserum.

Isolation and purification of the anti-PACAP monoclonal antibodies are conducted in accordance with methods for isolating and purifying immunoglobulin, similar to the isolation and purification of the polyclonal antibodies described above.

The anti-PACAP polyclonal antibody reactive to a partial region of PACAP can be prepared by the above-mentioned method using a peptide corresponding to the partial region thereof as a hapten for immunization. Further, such anti-PACAP polyclonal antibody can also be prepared from the anti-PACAP polyclonal antibody prepared by using PACAP as a hapten, by use of affinity chromatography employeing a column to which a peptide corresponding to the partial region thereof is bound.

Screening of hybridoma cells producing the anti-PACAP antibody reactive to a partial region of PACAP and hybridoma cells producing the anti-PACAP monoclonal antibody reactive to PACAP, but not reactive to the partial region thereof can be accomplished, for example, by assaying affinity of the peptide corresponding to the above partial region for the antibody produced by the hybridoma cells.

By using the anti-PACAP monoclonal and polyclonal antibodies obtained above, assay and tissue staining of PACAP can be carried out. For these purposes, antibody molecules themselves may be used, and F(ab')$_2$, Fab' or Fab fractions of the antibody molecules may be used.

PACAP is usually assayed by competitive methods which will be described below. It is however preferable to use sandwich methods for the reason described above.

In the competitive methods, the anti-PACAP antibody obtained in the present invention is competitively reacted with a test solution and labeled PACAP, followed by measurement of the ratio of labeled PACAP bound to the antibody, thereby determining the amount of PACAP contained in the test solution.

The labeling agents for PACAP or for antibodies described below include radioisotopes, enzymes, fluorescent substances and luminous substances. The radioisotopes include, for example, $^{125}$I, $^{131}$I, $^3$H and $^{14}$C. The enzymes which are stable and high in specific activity are preferably used. Examples of such enzymes include β-galactosidase, β-gulcosidase, alkaline phosphatase, peroxidase and malate dehydrogenase. The fluorescent substances include fluorescamine and fluorescein isothiocyanate. The luminous substances include luminol, luminol derivatives, luciferin and lucigenin. Further, a biotin-avidin system may also be used in order to bind the labeling agent to the antibody or PACAP.

When the activity of the above-mentioned labeling agents is assayed, it is necessary to separate labeled PACAP bound to the antibody from free labeled PACAP. This separation is hereinafter referred to as B/F separation for brevity. When the enzymes are used as the labeling agents, active adsorbents such as insolubilized antibodies to the anti-PACAP antibody or insolubilized protein A are advantageously used as reagents for the B/F separation. For example, an anti-IgG antibody (corresponding to the antibody to the anti-PACAP antibody) is used as the solid phase, and labeled PACAP binds to the anti-IgG antibody of the solid phase through the above-mentioned antibody reactive thereto to measure the labeling agent on the solid phase. When the enzymes are used as the labeling agents, the activity of the enzymes on an insolubilized carrier is assayed by ordinary colorimetric methods or fluorescent methods. When the radioisotopes and the like are used as the labeling agents, reagents such as antibodies to the anti-PACAP antibody which are not insolubilized, sodium sulfate, dextran charcoal powder and polyethylene glycol are used for the B/F separation, in addition to the above-mentioned reagents. In any methods, the activity of the labeling agent in the supernatant or in the precipitate is assayed.

The above-mentioned insolubilization may be achieved by physical adsorption or chemical bonding usually used to insolubilize or immobilize polysaccharides such as agarose, dextran and cellulose; synthetic resins such as polystyrene, polyacrylamide and silicone; and glass.

In the competitive methods, the anti-PACAP antibody, the test solution, labeled PACAP and the reagent for B/F separation can be reacted in any order. Also, all or a part of them may be reacted at the same time. It is however preferable that at least labeled PACAP is added to the reaction system simultaneously with the reaction of the test solution and the anti-PACAP antibody, or after the reaction. The reagents for the B/F separation such as sodium sulfate, dextran charcoal powder and polyethylene glycol are mainly added to the reaction system at the final stage thereof.

On the other hand, in the sandwich methods, the test solution is brought into contact with (or reacted with) the insolubilized anti-PACAP antibody (the primary reaction), and further the labeled anti-PACAP antibody is reacted therewith (the secondary reaction), followed by assay of the activity of the labeling agent on the insolubilized carrier, whereby the amount of PACAP in the test solution can be determined. The primary and secondary reactions may be conducted at the same time or at different time. The labeling agents and the insolubilizing methods can conform to those described above.

As the anti-PACAP antibody used in the secondary reaction, it is preferred to use the antibody different from the anti-PACAP antibody used in the primary reaction in the site to which PACAP binds.

Namely, the antibodies used in the primary and secondary reactions may be polyclonal or monoclonal antibodies, respectively. For example, however, when the antibody used in the primary reaction recognizes the C-terminal portion of PACAP38NH$_2$ (class IV), it is preferred to use in the secondary reaction the antibody which recognizes portions or regions other than the C-terminal portion, namely recognizes the N-terminal portion (class I), the region from the N-terminal portion to the central portion (class II) or the region from C-terminal portion to the central portion (class III).

In the sandwich immunoassays, both of the antibody for solid phase and the antibody for labeling may be antibodies of any class and subclass, and may be F(ab')$_2$, Fab' or Fab fractions which are obtained by removing Fc' or Fc fractions therefrom, as long as they have antibody activity.

In the sandwich immunoassays, when the monoclonal antibody is used, it is not always necessary to use one kind of antibody as the antibody for solid phase or for labeling. For the purpose of improving assaying sensitivity, mixtures of two or more kinds of antibodies can be used.

Further, the immunoassays using the antibodies which are obtained according to the present invention can be used for diagnosis and treatment of diseases related to PACAP.

Humors such as plasma, serum, urine, cerebrospinal fluid, ascites, pleural fluid and amniotic fluid, sputum and feces can be used as test samples. These samples can be used for the immunoassays as such or with concentration after dilution or extraction with various buffers.

Any buffers or organic solvents can be used as solvent for dilution or extraction of the samples. Preferred examples thereof include buffers for immunoassay, water, physiological saline, acetate buffer, acetone, chloroform-methanol and these solutions containing surface active agents. After extraction, the samples are sometimes heat treated. The samples may be concentrated directly under reduced pressure or under ordinary pressure in a stream of nitrogen. Also, the samples may be added to carriers for ion exchange or for reverse-phase chromatography, or to anti-PACAP antibody-bound carriers, and then eluted under appropriate conditions, followed by concentration under reduced pressure or under ordinary pressure in a stream of nitrogen. The carriers for reverse-phase chromatography includ C2, C8, C18 and phenyl cartridges. It is particularly preferable to use the anti-PACAP antibody-bound carriers as the carriers for concentration. Condensates are dissolved in the buffers for immunoassay, and then subjected to the immunoassays.

Further, the anti-PACAP antibodies obtained in the present invention can also be used for immunohistochemical station of PACAP. Methods thereof can be conducted, for example, in accordance with direct methods using the labeled anti-PACAP antibodies, and indirect methods using the anti-PACAP antibodies and the labeled antibodies to the anti-PACAP antibodies.

Furthermore, of the anti-PACAP antibodies obtained in the present invention, the antibody which can neutralize the adenylate cyclase activity of PACAP can be used as a specific neutralizing antibody.

As methods for screening an antibody specifically depressing the activity of PACAP from the anti-PACAP antibodies, any methods for detecting the parmacological activity of PACAP can be used. Examples of such methods include an in vitro assay system in which measurements are made based on the adenylate cyclase activity of PACAP in primary culture of hypophyses or in culture systems of various cells containing brown cytoma cell strain PC12h, and an in vivo assay system in which measurements are made based on the vasodepressor activity of PACAP to the experimental animals.

The antibodies specifically depressing the activity of PACAP may be antibodies of any class, such as IgG, IgA and IgM, and may be Fab' of Fab fractions which are obtained by removing Fc' or FC regions therefrom, or polymers of the fractions. A chimera antibody can also be used which is obtained by fusing a variable gene region of a monoclonal antibody being specifically capable of depressing the activity of PACAP with a constant gene region of human immunoglobulin, followed by expression as a recombinant.

Hybridoma cells obtained in Example 8 described below were deposited with the Institute for Fermentation, Osaka, Japan (IFO) on Feb. 27, 1990, and with the Fermentation Research Institute, the Agency of Industrial Science and Technology, the Ministry of International Trade and Industry, Japan (FRI) 1–3, Higashi-chome, Tsukuba-shi, Ibaraki-Kea 305 Japan on March 16, 1991, under the following accession numbers.

| Hybridoma cell | IFO | FERM-BP (FRI) |
| --- | --- | --- |
| PA-1N | 50225 | 2811 |
| PA-3N | 50226 | 2812 |
| PA-5N | 50227 | 2813 |
| PA-6N | 50228 | 2814 |
| PA-2C | 50229 | 2815 |
| PA-1C | 50230 | 2816 |

In the following Examples, antibodies obtained from the respective hybridoma cells are represented by giving a symbol "a" after the names of the cells.

REFERENCE EXAMPLE 1

Synthesis of PACAP38 $NH_2$

PACAP38 $NH_2$ was synthesized by using 1.04 g (0.5 mmole) of a commercially available p-methyl BHA resin (Applied Biosystems Inc.) and a peptide synthesizer (Model 430A, Applied Biosystems Inc.).

A starting amino acid, Boc-Lys(Cl-Z), was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP38:

Boc-Asn, Boc-Lys(Cl-Z), Boc-Val, Boc-Arg(Tos), Boc-Gln, Boc-Tyr(Br-Z), Boc-Gly, Boc-Leu, Boc-Ala, Boc-Met, Boc-Ser(Bzl), Boc-Asp(OBzl), Boc-Thr(Bzl), Boc-Phe, Boc-Ile, and Boc-His(Tos)

After the completion of each reaction, the residual amino groups were acetylated with acetic anhydride to obtain 2.42 g of a protected PACAP38 $NH_2$ resin.

0.51 g of the resulting protected PACAP38 $NH_2$ resin was treated with 5 ml of hydrogen fluoride in the presence of 0.6 g of p-cresol at 0° C. for 60 minutes, followed by removal of excess hydrogen fluoride by distillation under reduced pressure. The residue was washed twice with 5 ml of ethyl ether, and then extracted with 6 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×90 cm) for elution with 50% acetic acid. The main fractions were collected, followed by removal by distillation under reduced pressure. Then, the residue was dissolved in 100 ml of 0.1% aqueous trifluoroacetic acid. The resulting solution was subjected to a YMC-ODS AM120 S-50 resin column (1.6×7 cm) and eluted by a linear gradient of 0.1% aqueous trifluoroacetic acid and 50% acetonitrile containing 0.1% trifluoroacetic acid.

The main fractions were combined, followed by lyophilization. Thus, 60 mg of white powder was obtained. This powder was dissolved in 20 ml of 0.05M aqueous ammonium acetate. The resulting solution was subjected to a CM-Cellulofine resin column (1×6 cm) and eluted by a linear gradient of from 0.05M to 1M ammonium acetate. The main fractions were combined. The combined solution was subjected to a YMC-ODS column (2.6×7 cm) again and eluted by a linear gradient of from 0% to 40% aqueous acetonitrile containing 0.1% trifluoroacetic acid. The fractions of 28% to 30% acetonitrile were collected, followed by lyophilization. Thus, 21.6 mg of white powder was obtained.

Anal. for amino acids: Asp 2.90(3), Thr 0.84(1), Ser 2.10(3), Glu 2.21(2), Gly 2.00(2), Ala 3.29(3), Val 3.19(3), Met 1.01(1), Ile 0.87(1), Leu 2.19(2), Tyr 3.93(4), Phe 0.92(1), Lys 7.18(7), His 0.96(1), Arg 4.19(4) $(M+H)^+$ by mass spectrography (SIMS): 4530 HPLC elution time: 19.6 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 50 minutes Flow rate: 1.0 ml/minute

REFERENCE EXAMPLE 2

Synthesis of PACAP27 $NH_2$

PACAP27 $NH_2$ was synthesized by using 1.04 g (0.5 mmole) of a commercially available p-methyl BHA resin (Applied Biosystems Inc.) and a peptide synthesizer (Model 430A, Applied Biosystems Inc.).

A starting amino acid, Boc-Leu, was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP38 (1–27):

Boc-Val, Boc-Ala, Boc-Leu, Boc-Tyr(Br-Z), Boc-Lys(Cl-Z), Boc-Met, Boc-Gln, Boc-Arg(Tos), Boc-Ser(Bzl), Boc-Asp(OBzl), Boc-Thr(Bzl), Boc-Phe, Boc-Ile, and Boc-His(Tos)

After the completion of each reaction, the residual amino groups were acetylated with acetic anhydride to obtain 2.31 g of a protected PACAP27 $NH_2$ resin.

0.79 g of the resulting protected PACAP27 $NH_2$ resin was treated with 10 ml of absolute hydrogen fluoride in the presence of 1.2 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 0.1% aqueous trifluoroacetic acid and 50% acetonitrile containing 0.1% trifluoroacetic acid. The main fractions were combined and the combined solution was applied onto a YMC-ODS column (2.6×7 cm) again and eluted by a linear concentration gradient with from 15 to 35% aqueous acetonitrile solution containing 0.1% trifluoroactetic acid. The acetonitrile 30 to 32% fractions were collected, followed by lyophilization. The resulting product was dissolved in 20 ml of 0.05M-aqueous ammonium acetate. The solution was applied onto a CM—Cellulofine resin column (1×6 cm) and eluted by a linear concentration gradient with water to 0.33M—aqueous ammonium acetate.

The main fractions (0.18 to 0.22M) were collected, followed by lyophilization. Thus, 20 mg of white powder was obtained.

Anal. for amino acids: Asp 1.96(2), Thr 0.94(1), Ser 2.57(3), Glu 1.07(1), Gly 0.95(1), Ala 3.00(3), Val 1.96(2), Met 0.88(1), Ile 0.88(1), Leu 1.93(2), Tyr 2.87(3), Phe 0.90(1), Lys 2.91(3), His 0.94(1), Arg 2.17(2) (M+H)$^+$ by mass spectrography (SIMS): 3146.7 HPLS elution time: 21.2 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 50 minutes Flow rate: 1.0 ml/minute

REFERENCE EXAMPLE 3

Synthesis of PACAP27 OH (His ser Asp Gly Ile Phe Thr Asp Ser Tyr Ser Arg Tyr Arg Lys Gln Met Ala Val Lys Lys Tyr Leu Ala Ala Val Leu-OH) (amino acid numbers 1–27 of SEQ ID NO:1).

PACAP27 OH was synthesized by using 0.60 g (0.5 mmole) of a commercially available Boc-Leu-OCH$_2$-PAM resin (Applied Biosystems Inc.) and a peptide synthesizer (Model 430A, Applied Biosystems Inc.).

The Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP27:

Boc-Val, Boc-Lys(Cl-Z), Boc-Arg(Tos), Boc-Gln, Boc-Tyr(Br-Z), Boc-Gly, Boc-Leu, Boc-Ala, Boc-Met, Boc-Ser(Bzl), Boc-Asp(OBzl), Boc-Thr(Bzl), Boc-Phe, Boc-Ile, and Boc-His(Tos)

After the additional condensation by the amino acids activated by DCC or HOBt/DCC, the unreacted amino groups were acetylated with acetic anhydride to obtain 1.25 g of a protected PACAP27 OH resin.

0.65 g of the resulting protected PACAP27-OCH$_2$-PAM resin was treated with 6 ml of absolute hydrogen fluoride in the presence of 1.0 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 0.1% aqueous trifluoroacetic acid and 50% acetonitrile containing 0.1% trifluoroacetic acid. The main fractions were combined and the combined solution was applied onto a YMC-ODS column (2.6×7 cm) again and eluted by a linear concentration gradient with from 15 to 40% aqueous acetonitrile solution containing 0.1% trifluoroactetic acid. The acetonitrile 25 to 28% fractions were collected, followed by lyophilization. The resulting product was dissolved in 20 ml of 0.05M-aqueous ammonium acetate. The solution was applied onto a CM—Cellulofine resin column (1×6 cm) and eluted by a linear concentration gradient with 0.05M to 0.33M—aqueous ammonium acetate.

The main fractions were collected, followed by lyophilization. Thus, 20 mg of white powder was obtained.

Anal. for amino acids: Asp 2.03(2), Thr 0.96(1), Ser 2.66(3), Glu 1.08(1), Gly 1.01(1), Ala 305(3), Val 1.98(2), Met 0.94(1), Ile 0.94(1), Leu 2.00(2), Tyr 2.96(3), Phe 0.95,(1), Lys 2.99(3), His 1.03(1), Arg 2.25(2) (M+H)$^+$ by mass spectrography (SIMS): 3147.9 HPLS elution time: 18.69 minutes Column conditions Column: YMC-ODS (AM-301, S-5 120A) (4.6×100) Eluent: A (0.1% aqueous trifluoroacetic acid) B (acetonitrile containing 0.1% trifluoroacetic acid) A linear gradient elution from the eluent A to the eluent B for 25 minutes Flow rate: 1.0 ml/minute

EXAMPLE 1-1

Synthesis of PACAP(14–38) NH$_2$

PACAP(14–38) NH$_2$ was synthesized by using 1.04 g (0.5 mmole) of a commercially available p-methyl BHA resin (Applied Biosystems Inc.) and a peptide synthesizer (Model 430A, Applied Biosystems Inc.).

A starting amino acid, Lys(Cl-Z), was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP(14–38) NH$_2$:

Boc-Asn, Boc-Lys(Cl-Z), Boc-Val, Boc-Arg(Tos), Boc-Gln, Boc-Tyr(Br-Z), Boc-Gly, Boc-Leu, Boc-Ala, Boc-Met

After the additional condensation by the amino acids activated by DCC or HOBt/DCC, the unreacted amino groups were acetylated with acetic anhydride to obtain 2.00 g of a protected PACAP(14–38) NH$_2$ resin.

0.48 g of the resulting protected PACAP(14–38) NH$_2$ resin was treated with 5 ml of absolute hydrogen fluoride in the presence of 0.48 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 0.1% aqueous trifluoroacetic acid and 30% acetonitrile containing 0.1% trifluoroacetic acid. The main fractions were collected, followed by lyophilization. Thus, 20.2 mg of white powder was obtained.

Anal. for amino acids: Asp 1.01(1), Glu 2.01(2), Gly 1.00(1), Ala 3.01(3), Val 2.85(3), Met 0.86(1), Leu 2.08(2), Tyr 1.98(2), Lys 6.37(7), Arg 3.24(3) $(M+H)^+$ by mass spectrography (SIMS): 3003.6 HPLS elution time: 13.1 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 25 minutes Flow rate: 1.0 ml/minute

EXAMPLE 1-2

Synthesis of PACAP(1–13) OH

PACAP(1–13) OH was synthesized by using 0.87 g (0.5 mmole) of a commercially available Boc-Tyr(Br-Z)-OCH$_2$-PAM resin (Applied Biosystems Inc.) and a peptide synthesizer (Model 430A, Applied Biosystems Inc.).

The Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP(1–13):

Boc-Arg(Tos), Boc-Tyr(Br-Z), Boc-Gly, Boc-Ser(Bzl), Boc-Asp(OBzl), Boc-Thr(Bzl), Boc-Phe, Boc-Ile, and Boc-His(Tos)

After the additional condensation by the amino acids activated by DCC or HOBt/DCC, the unreacted amino groups were acetylated with acetic anhydride to obtain 1.86 g of a protected PACAP(1–13)OCH$_2$-PAM resin.

0.70 g of the resulting protected resin was treated with 10 ml of absolute hydrogen fluoride in the presence of 0.81 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 0.1% aqueous trifluoroacetic acid and 33% acetonitrile containing 0.1% trifluoroacetic acid. The main fractions were combined and the combined solution was purified again under the same column conditions. The main fractions were collected, followed by lyophilization. Thus, 38 mg of white powder was obtained.

Anal. for amino acids: Asp 2.00(2) , Thr 0.93(1) , Ser 2.43(3) , Glu 1.05(1) , Gly 1.00(1), Tyr 1.82(2), Phe 1.02(1), His 1.31(1), Arg 1.12(1) $(M+H)^+$ by mass spectrography (SIMS): 1547.5 HPLS elution time: 12.3 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 25 minutes Flow rate: 1.0 ml/minute

EXAMPLE 1-3

Synthesis of PACAP(4–27) OH

PACAP(4–27) OH was synthesized by using 0.60 g (0.5 mmole) of a commercially available Boc-Leu-OCH$_2$-PAM resin (Applied Biosystems Inc.) and a peptide synthesizer (Model 430A, Applied Biosystems Inc.).

The Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP(4–27):

Boc-Lys(Cl-Z), Boc-Val, Boc-Arg(Tos), Boc-Gln, Boc-Tyr(Br-Z), Boc-Gly, Boc-Leu, Boc-Ala, Boc-Met, Boc-Ser(Bzl), Boc-Asp(OBzl), Boc-Thr(Bzl), Boc-Phe, Boc-Ile

After the additional condensation by the amino acids activated by DCC or HOBt/DCC, the unreacted amino groups were acetylated with acetic anhydride to obtain 1.08 g of a protected PACAP(4–27)OCH$_2$-PAM resin.

0.29 g of the resulting protected resin was treated with 5 ml of absolute hydrogen fluoride in the presence of 0.49 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml under reduced pressure. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 15% acetonitrile containing 0.1% trifluoroacetic acid and 50% acetonitrile containing 0.1% trifluoroacetic acid. The main fractions were collected, followed by lyophilization to obtain 33 mg of white powder. The powder was dissolved in 20 ml of 0.05M-aqueous ammonium acetate. The solution was applied onto a CM-Cellurofine resin column (1×6 cm) and eluted by a linear gradient with water to 0.30M-aqueous ammonium acetate. The main fractions (0.18 to 0.22M) were collected, followed by lyophilization. Thus, 33 mg of white powder was obtained.

Anal. for amino acids: Asp 1.02(1) , Thr 0.98(1) , Ser 1.78(3) , Glu 1.07(1) , Gly 1.02(1) , Ala 3.04(3) , Val 1.89(2) , Met 0.81(1) , Ile 0.89(1), Leu 2.00(2), Tyr 2.91(3), Phe 0.90(1), Lys 2.89(3), Arg 2.20(2) $(M+H)^+$ by mass spectrography (SIMS): 2808.5 HPLS elution time: 14.5 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 35 minutes Flow rate: 1.0 ml/minute

EXAMPLE 1-4

Synthesis of PACAP(31–38) NH$_2$

PACAP(31–38) NH$_2$ was synthesized by using 0.98 g (0.5 mmole) of a commercially available p-methyl BHA resin (Applied Biosystems Inc.) and a peptide synthesizer (Model 430A, Applied Biosystems Inc.).

A starting amino acid, Boc-Lys(Cl-Z), was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of PACAP(14–38) NH$_2$:

Boc-Asn, Boc-Lys(Cl-Z), Boc-Val, Boc-Arg(Tos), Boc-Gln, Boc-Tyr(Br-Z)

After the additional condensation by the amino acids activated by DCC or HOBt/DCC, the unreacted amino groups were acetylated with acetic anhydride to obtain 2.00 g of a protected PACAP(31–38) NH$_2$ resin.

0.43 g of the resulting protected PACAP(31–38) NH$_2$ resin was treated with 5 ml of absolute hydrogen fluoride in the presence of 0.6 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin Column (2.6×7 cm) and eluted by a liner gradient of 0.1% aqueous trifluoroacetic acid and 33% acetonitrile containing 0.1% trifluoroacetic acid. The main fractions were collected, followed by lyophilization. Thus, 45 mg of white powder was obtained.

Anal. for amino acids: Asp 1.02(1), Glu 1.05(1), Val 1.00(1), Tyr 0.90(1), Lys 2.98(3), Arg 1.12(1) (M+H)$^+$ by mass spectrography (SIMS): 1062.7 HPLS elution time: 11.6 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent mixture [A:B(4:1)] for 20 minutes Flow rate: 1.0 ml/minute

EXAMPLE 1-5

Synthesis of [Cys$^{10}$]PACAP(11–27) NH$_2$

[Cys$^{10}$]PACAP(11–27) NH$_2$ was synthesized by using 0.66 g (0.5 mmole) of a commercially available p-methyl BHA resin (Applied Biosystems Inc.) and a peptide synthesizer (Model 430A, Applied Biosystems Inc.).

A starting amino acid, Boc-Leu, was activated with HOBt/DCC and then condensed to the resin. Thereafter, the Boc group on the resin was treated with 50% trifluoroacetic acid/methylene chloride to deprotect the amino group. To this free amino group, the following protected amino acids activated with HOBt/DCC were condensed in turn according to the amino acid sequence of [Cys$^{10}$]PACAP(11–27) NH$_2$:

Boc-Val, Boc-Ala, Boc-Tyr(Br-Z), Boc-Lys(Cl-Z), Boc-Met, Boc-Gln, Boc-Arg(Tos), Boc-Ser(Bzl), Boc-Cys(MeBzl)

After the additional condensation by the amino acids activated by DCC or HOBt/DCC, the unreacted amino groups were acetylated with acetic anhydride to obtain 1.20 g of a protected [Cys$^{10}$]PACAP(11–27) NH$_2$ resin.

0.60 g of the resulting protected resin was treated with 10 ml of absolute hydrogen fluoride in the presence of 1.0 g of p-cresol at 0° C. for 60 minutes, followed by removal of excess hydrogen fluoride by distillation under reduced pressure. The residue was washed twice with 5 ml of ethyl ether, and then extracted with 5 ml of 50% aqueous acetic acid. The insoluble material was removed by filtration and washed with 5 ml of 50% aqueous acetic acid. The filtrate and the washings were combined, and the combined solution was concentrated to 2 to 3 ml. The concentrated solution was applied on a Sephadex LH-20 column (2×75 cm) for elution with 50% acetic acid. The main fractions were collected, followed by distillation under reduced pressure. The residue was dissolved in 100 ml of 0.1% aqueous trifluoroacetic acid. The resulting solution was subjected to a YMC-ODS AM120 S-50 resin column (2.6×7 cm) and eluted by a liner gradient of 0.1% aqueous trifluoroacetic acid and 50% acetonitrile containing 0.1% trifluoroacetic acid. The main fractions were collected, followed by lyophilization. Thus, 70 mg of white powder was obtained.

Anal. for amino acids: Ser 0.92(1), Glu 1.07(1), Ala 2.00(2), Val 1.96(2), Met 0.88(1), Leu 1.93(2), Tyr 1.87(2), Lys 2.91(3), Arg 2.17(2) (M+H)$^+$ by mass spectrography (SIMS): 2127.9 HPLS elution time: 20.8 minutes Column conditions Column: YMC-ODS (AM-301, S-5 120A) Eluent: A (0.1% aqueous trifluoroacetic acid) B (acetonitrile containing 0.1% trifluoroacetic acid) A linear gradient elution from the eluent A to the eluent B for 50 minutes Flow rate: 1.0 ml/minute

EXAMPLE 2-1

Preparation of Immunogen Containing PACAP38NH$_2$

A complex comprising PACAP38NH$_2$ obtained in Reference Example 1 described above and bovine thyroglobulin (hereinafter referred to as BTG) was prepared, and it was used as an immunogen.

Namely, 2.8 mg of PACAP38NH$_2$ and 8.4 mg of BTG were dissolved in 1 ml of 0.1M phosphate buffer (pH 6.9), and glutaraldehyde was added thereto to a final concentration of 0.04%, followed by reaction at room temperature for 2 hours. After reaction, the resulting product was dialyzed against physiological saline at 4° C. for 2 days.

EXAMPLE 2-2

Preparation of Immunogen Containing PACAP(11–27)NH$_2$

A complex comprising [Cys$^{10}$]PACAP(11–27)NH$_2$ obtained in Example 1-5 described above and BTG was prepared, and it was used as an immunogen.

Namely, 20 mg of BTG was dissolved in 1.4 ml of 0.1M phosphate buffer (pH 6.9). The resulting solution was mixed with 100 μl of a DMF solution containing 2.2 mg (8 μmoles) of N-(γ-maleimidobutyryloxy)succinimide (hereinafter referred to as GMBS), followed by reaction at room temperature for 40 minutes. After reaction, the resulting product was fractionated on a Sephadex G-25 column, thereby obtaining a maleimide group-introduced BTG. Then, 12 mg of the maleimide group introduced BTG and 3.0 mg of [Cys$^{10}$]PACAP(11–27)NH$_2$ were mixed and reacted with each other at 4° C. for 3 days. After reaction, the reaction product was dialyzed against physiological saline at 4° C. for 2 days.

EXAMPLE 3-1

Immunization of PACAP38NH$_2$-BTG Conjugate

The female mice BALB/C 6 to 8 weeks old were subcutaneously immunized with 80 μg/mouse of the immunogen PACAP38NH$_2$-BTG complex, obtained in Example 2-1 described above, together with Freund's complete adjuvant. Then, the mice were additionally immunized with the same amount of the immunogen, together with Freund's incomplete adjuvant, 2 to 3 times at 4-week intervals.

EXAMPLE 3-2

Immunization of PACAP(11–27)NH$_2$-BTG Conjugate

The male rabbits were subcutaneously immunized with 400 μg/rabbit of the PACAP(11–27)NH$_2$-BTG complex, obtained in Example 2-2 described above, together with Freund's complete adjuvant. Then, the rabbits were additionally immunized with the same amount of the immunogen, together with Freund's incomplete adjuvant, 6 times at 4-week intervals.

EXAMPLE 4-1

Preparation of Horseradish Peroxidase (HRP)-Labeled PACAP38NH$_2$

A marker for the enzyme immunoassay (EIA) was prepared by crosslinking PACAP38NH$_2$ obtained in Reference Example 1 and HRP.

Namely, 180 nmoles of PACAP38NH$_2$ was dissolved in 500 μl of 0.1M phosphate buffer (pH 6.8), and 50 μl of a DMF solution containing 450 nmoles of GMBS was mixed therewith, followed by reaction at room temperature for 30 minutes. After reaction, the resulting product was fractionated on a Sephadex G-15 column. Thus, 100 nmoles of a maleimide group-introduced polypeptide was obtained.

On the other hand, 7.9 mg (200 nmoles) of HRP was dissolved in 0.95 ml of 0.02M phosphate buffer (pH 6.8) containing 0.15M NaCl, and 50 μl of a DMF solution containing 1.54 mg (4.9 μmoles) of N-succinimidyl-3-(2-pyridylthio)propionate (hereinafter referred as SPDP) was mixed therewith, followed by reaction at room temperature for 40 minutes. After reaction, 0.33 ml of 0.1M acetate buffer (pH 4.5) containing 8.2 mg (53 μmoles) of dithiothreitol was added thereto, followed by reaction at room temperature for 20 minutes. Then, the reaction product was fractionated on a Sephadex G-25 column. Thus, 6 mg (100 nmoles) of a SH group-introduced enzyme was obtained.

Then, 100 nmoles of maleimide group-introduced PACAP38NH$_2$ and 100 nmoles of SH group-introduced HRP were mixed and reacted with each other at 4° C. for 16 hours. After reaction, the reaction product was fractionated on an Ultrogel AcA44 (LKB-Pharmacia) to obtain HRP-labeled PACAP38NH$_2$.

EXAMPLE 4-2

Preparation of HRP-Labeled PACAP(11–27)NH$_2$

In 950 μl of 180 nmoles of 0.1M phosphate buffer (pH 6.8) was dissolved 8 mg (200 nmoles) of HRP, and 50 μl of a DMF solution containing 1.4 mg (5 μnmoles) of GMBS was mixed therewith, followed by reaction at room temperature for 40 minutes. Thereafter, the resulting product was fractionated on a Sephadex G-15 column to obtain maleimide group-introduced HRP. Then, 3.3 mg (78 nmoles) of maleimide group-introduced HRP thus prepared and 0.65 mg (310 nmoles) of [Cys$^{10}$]PACAP(11–27)NH$_2$ prepared in Example 1-5 were mixed and reacted with each other at 4° C. for 1 day. After reaction, the reaction product was fractionated on an Ultrogel AcA44 (LKB-Pharmacia) to obtain HRP-labeled [Cys$^{10}$]PACAP(11–27)NH$_2$.

EXAMPLE 5-1

Determination of Antibody Titer of Mouse Antiserum

The antibody titer of the mouse antiserum was determined by the following method. In order to prepare an anti-mouse immunoglobulin antibody-bound microplate, 100 μl of 0.1M carbonate buffer (pH 9.6) containing 100 μg/ml of the anti-mouse immunoglobulin antibody [IgG fraction, Kappel) was first poured into each well of a 96-well microplate, and the plate was allowed to stand at 4° C. for 24 hours. After the plate was washed with phosphate buffered saline (hereinafter referred to as PBS), 300 μl of PBS containing 25% Blockace (Snow Brand Milk Products) was poured into each well to block excess binding sites of the wells, and treated at a temperature of at least 4° C. for 24 hours.

To each well of the above-mentioned anti-mouse immunoglobulin antibody-bound microplate were added 50 μl of buffer E [0.02M phosphate buffer (pH 7.0) containing 10% Blockace, 2 mg/ml bovine serum albumin (hereinafter referred to as BSA), 0.4M NaCl, 2 mM EDTA and 0.1% NaN$_3$] and 50 μl of the mouse anti-PACAP38NH$_2$ antiserum diluted with buffer E, followed by reaction at 4° C. for 16 hours. After the plate was washed with PBS, 100 μl of the HRP-labeled PACAP38NH$_2$ prepared in Example 4-1 described above [diluted 100 times with buffer H (pH 7.0) containing 2 mg/ml BSA and 0.15M NaCl was added to each well, followed by reaction at room temperature for 6 hours. After reaction, the plate was washed with PBS, and then 100 μl of 0.1M citrate buffer (pH 5.5) containing 0.2% o-phenylenediamine and 0.02% hydrogen peroxide was poured into each well to assay the enzyme activity on the solid phase, followed by reaction at room temperature for 10 minutes. After 100 μl of 4N sulfuric acid was added thereto to terminate the reaction, the absorption at 492 nm was measured by a plate reader (MTP-32, Corona).

The results are shown in FIG. 1. Increases in anti-PACAP38 antibody titer were observed in 4 mice of the 8 immunized mice.

EXAMPLE 5-2

Determination of Antibody Titer of Rabbit Antiserum

The antibody titer of the rabbit antiserum was determined in a similar manner. An anti-rabbit immunoglobulin antibody (IgG fraction, Kappel)-bound microplate was prepared in the same manner as with Example 5-1 described above. To each well of the above plate were added 50 μl of buffer E and 50 μl of the rabbit anti-PACAP(11–27)NH$_2$ antiserum diluted with buffer E, followed by reaction at 4° C. for 16 hours. After the plate was washed with PBS, 100 μl of HRP-labeled PACAP(11–27)NH$_2$ prepared in Example 4-2 described above [diluted 200 times with buffer H was added to each well, followed by reaction at room temperature for 6 hours. After reaction, the plate was washed with PBS, and then the enzyme activity on the solid phase was assayed by the use of the TMB microwell peroxidase substrate system (Kirkegaaed & Perry Lab., Inc., sold by Funakoshi Yakuhin). A plate reader (MTP-32, Corona) was used for measurement of the absorbance (at 450 nm).

The results are shown in FIG. 2. High antibody titer was detected in all of the immunized rabbits.

EXAMPLE 6

Cell Fusion

Mouse No. 5 which showed relatively high antibody titer was inoculated with a solution prepared by dissolving 200 μg of the immunogen in 0.25 ml of physiological saline to conduct the final immunization. The spleen was taken out of the mouse after 3 days from the final immunization, pressed by a stainless mesh, filtered, and floated in Eagle's minimum essential medium (MEM), thereby obtaining a spleen cell-floating solution. As a cell for cell fusion, BALB/C mouse-derived myeroma cell P3-X63.Ag8.U1 (P3U1) was used [*Current Topics in Microbiology and Immunology* 81, 1 (1978)]. The cell fusion was carried out in accordance with the original method [*Nature* 256, 495 (1957)]. Namely, the spleen cells and the P3U1 cells were washed 3 times with serum-free MEM, and mixed with each other so that the number ratio of the spleen cells to the P3U1 cells reached 5:1. The mixture was centrifuged at 800 rpm for 15 minutes to precipitate the cells. After the supernatant was thoroughly removed, the precipitate was lightly loosened, and 0.3 ml of 45% polyethylene glycol (PEG) 600 (Kochlight) was added thereto. Then, the mixture was allowed to stand in a hot water bath at 37° C. for 7 minutes to perform the fusion. After the fusion was completed, MEM was added to the cells at a rate of 2 ml per minute. After 12 ml of MEM was added in total, the supernatant was removed by centrifugation at 600 rpm for 15 minutes. The resulting precipitate was floated in GIT medium (GIT-10FCS, Wako Pure Chemical Industries) containing 10% fetal calf serum so that the P3U1 cells were contained in an amount of 2×10$^6$ cells/ml. The resulting suspension was seeded in 120 wells of a 24-well multi-dish (Linbro) in an amount of 1 ml/well. After seeding, the cells were incubated in a 5% carbon dioxide incubator at 37° C. After 24 hours, 1 ml of GIT-10FCS medium (HAT medium) containing HAT (1×10$^{-4}$M hypoxanthine, 4×10$^{-7}$M aminopterin and 1.6×10$^{-3}$M thymidine) was added to each well to initiate HAT selective culture. The HAT selective culture was continued by discarding 1 ml of old liquor and then supplying 1 ml of HAT medium, 3, 6 and 9 days after the initiation of the culture. The proliferation of hybridoma cells was observed 9 to 14 days after the completion of the cell fusion. When the culture solution turned yellow (about 1×10$^5$ cells/ml), the supernatants were recovered and the antibody titer was assayed.

EXAMPLE 7

Screening of Hybridoma Cell

To the anti-mouse immunoglobulin antibody-bound microplate were added 50 μl of buffer E and 50 μl of the hybridoma culture supernatant, followed by reaction at room temperature for 6 hours. After the plate was washed with PBS, 100 μl of the HRP-labeled PACAP38NH$_2$ prepared in Example 4 described above (diluted 200 times with buffer H) was added thereto, followed by reaction at 4° C. for 16 hours. After the plate was washed with PBS, the enzyme activity on the solid phase was assayed by the method described in Example 5-1 described above.

The supernatants of all of the 120 wells in which the proliferation of the cells was observed were thus examined. As a result, antibody titer was detected in 18 wells.

EXAMPLE 8

Cloning

Of the wells which showed positive antibody activity, the hybridoma cells contained in the wells of Nos. 44, 49, 97 and 113 were cloned by the limiting dilution method. Namely, the hybridoma cells were floated in RPMI 1640-20FCS so as to be contained in an amount of 1.5 cells/ml, and 2.0 ml thereof was poured into each well of a 96-well microplate (Nunk). In pouring, the thymocytes of BALB/C mice were added thereto as feeder cells so as to be contained in an amount of 5×10$^5$ cells/well. After about one week, the proliferation of the cells was observed. The antibody titer of the supernatants was examined by the EIA described in Example 5. As a result, antibodies were produced in 28 clones of 30 clones for the hybridoma cells of No. 44, in 47 clones of 50 clones for the hybridoma cells of No. 49, in 49 clones of 50 clones for the hybridoma cells of No. 97 and in 48 clones of 50 clones for the hybridoma cells of No. 113. Of these clones, giving attention to clone PA-6N obtained from No. 44-2 and monoclonal antibody PA-6Na produced thereby, clone PA-1N obtained from No. 49-3 and monoclonal antibody PA-1Na produced thereby, clone PA-2C obtained from No. 97-2 and monoclonal antibody PA-2Ca produced thereby, and clone PA-5N obtained from No. 113-5 and monoclonal antibody PA-5Na produced thereby, the following experiments were made.

Similarly, the cell fusion experiment was conducted using the spleen cells of another mouse during immunization. Giving attention also to clone PA-1C obtained from No. 28-12 and monoclonal antibody PA-1Ca produced thereby, and clone PA-3N obtained from No. 10-3 and monoclonal antibody PA-3Na produced thereby, the following experiment was carried out.

EXAMPLE 9

Preparation of Large Amount of Monoclonal Antibodies

The mice which had been given 0.5 ml of mineral oil intraperitoneally or the untreated mice (BALB/C) were injected intraperitoneally with 1 to 3×10$^5$ cells/mouse of the above-mentioned hybridoma cells, and then the antibody-containing ascites was recovered after 6 to 20 days.

EXAMPLE 10

Purification of Monoclonal Antibodies

The monoclonal antibodies were purified by a protein-A column or a diethylaminoethyl (DEAE)-cellulose column from the ascites obtained in Example 9 described above.

Namely, 6 ml of the ascites containing PA-1N was diluted with the same amount of a binding buffer (pH 9.0, 1.5M glycine containing 3.5M NaCl and 0.05% NAN$_3$). The resulting solution was subjected to a protein-A Sepharose (Pharmacia) column which had been pre-equilibrated with the binding buffer, and a specific antibody was eluted with an eluting buffer (pH 3.0, 0.1M citrate buffer containing 0.05% NAN$_3$). By the above procedures, 28 mg of the specific antibody was obtained.

Similarly, 23 mg of a specific antibody was obtained from 5 ml of the ascites containing PA-5N, 13 mg of a specific antibody was obtained from 7.5 ml of the ascites containing PA-6N, and 45 mg of a specific antibody was obtained from 14 ml of the ascites containing PA-1C.

On the other hand, a saturated ammonium sulfate solution was added to 20 ml of the ascites containing PA-3N to a final concentration of 45% for salt precipitation, followed by centrifugation (20,000 g, 30 minutes). The precipitate fraction was dialyzed against 0.02M borate buffer (pH 7) containing 0.15M NaCl (hereinafter referred to as BBS), and further dialyzed against 0.01M phosphate buffer containing 0.01M NaCl. The antibody fraction was loaded on a DEAE cellulose column (DE-52, Wattman, 2.5 cm in diameter×10 cm), and eluted by a linear concentration gradient (0.01M–0.35M) of 100 ml of NaCl. By the above procedures, 136 mg of a specific antibody was obtained.

Similarly, 57 mg of a specific antibody was obtained from 7.5 ml of the ascites containing PA-2C.

EXAMPLE 11

Determination of Class and Subclass of Monoclonal Antibody

Into each well of a 96-well microplate was poured 100 μl of 0.1M carbonate buffer (pH 9.6) containing 5 μg/ml of PACAP38NH$_2$ prepared above, and the microplate was allowed to stand at 4° C. for 24 hours. The excess binding sites of the wells were blocked with Blockace according to the method described in Example 5-1 to prepare a PACAP38 NH$_2$-bound plate. Then, each of supernatants of PA-1N, PA-3N, PA-5N, PA-6N, PA-2C and PA-1C was added to each well of the plate in an amount of 100 μl, followed by reaction at room temperature for 3 hours. Then, the class and subclass were examined by the enzyme-linked immunosorbent assay (ELISA) using an isotype typing kit (Mouse-Typer™ Sub-Isotyping Kit, Bio RAD). As a result, PA-1Na, PA-6Na, PA-2Ca and PA-1Ca belonged to IgG1, κ, PA-5Na belonged to IgG2a, κ, and PA-3Na belonged to IgG2b, κ.

EXAMPLE 12

Preparation of F(ab')$_2$ Fraction

PA-6Na described in Example 10 was concentrated to 8 mg/500 μl by a Collodion bag (Emuesu Kiki), and then dialyzed against 0.1M acetate buffer containing 0.1M NaCl. To the resulting antibody solution was added 0.4 mg of pepsin (crystallized twice, Sigma), followed by reaction at 37° C. for 16 hours. Then, the F(ab')$_2$ fraction was purified by an FPLC (Pharmacia) using a Superrose 12 column equilibrated with 0.1M phosphate buffer (pH 6.8).

By a similar technique, 0.445 mg of pepsin was added to 8.9 mg of PA-1Ca described in Example 10 to prepare the F(ab') fraction.

EXAMPLE 13

Preparation of HRP-Labeled Anti-PACAP Monoclonal Antibodies (1) PA-6Na F(ab')$_2$-HRP To 1 ml of a solution containing 2.2 mg (22 nmoles)/ml of the PA-6Na F(ab')$_2$ fraction described in Example 12 was added 50 μl of a DMF solution containing 260 nmoles of GMBS, followed by reaction at room tempedrature for 40 minutes. The reaction solution was fractionated on a Sephadex G-25 column [1 cm in diameter×30 cm, eluent: 0.1M phosphate buffer (pH 6.7)] to obtain a maleimide group-introduced F(ab')$_2$ fraction. With 1.5 mg of the resulting F(ab')$_2$ fraction was mixed 5.5 mg of SH group-introduced HRP prepared by the method described in Example 4-1, and the reaction product was concentrated to about 0.3 ml by a collodion bag, followed by standing at 4° C. for 16 hours. The reaction solution was loaded on an Ultrogel AcA34 column (10 mm in diameter×40 mm) to purify an F(ab')$_2$-HRP complex fraction. It was confirmed from the absorbance at 280 nm and 403 nm that HRP was introduced in an amount of 2.4 molecules/molecule of F(ab')$_2$.

(2) PA-1Ca F(ab')$_2$-HRP

In a similar manner, an F(ab')$_2$-HRP complex was prepared by using 2.9 mg of the PA-1Ca F(ab')$_2$ fraction described in Example 12.

(3) PA-2Ca IgG-HRP

To 6.4 mg (43 nmoles) of the PA-2Ca purified fraction described in Example 10 was added 15-fold moles of GMBS, followed by introduction of a maleimide group. Then, the resulting product was reacted with SH group-introduced HRP in a similar manner to prepare a marker into which HRP was introduced in an amount of 2.4 molecules/molecule of IgG.

EXAMPLE 14

Competitive Method-EIA (1) Competitive Method-EIA Using PA-1Na

Figure 3A:
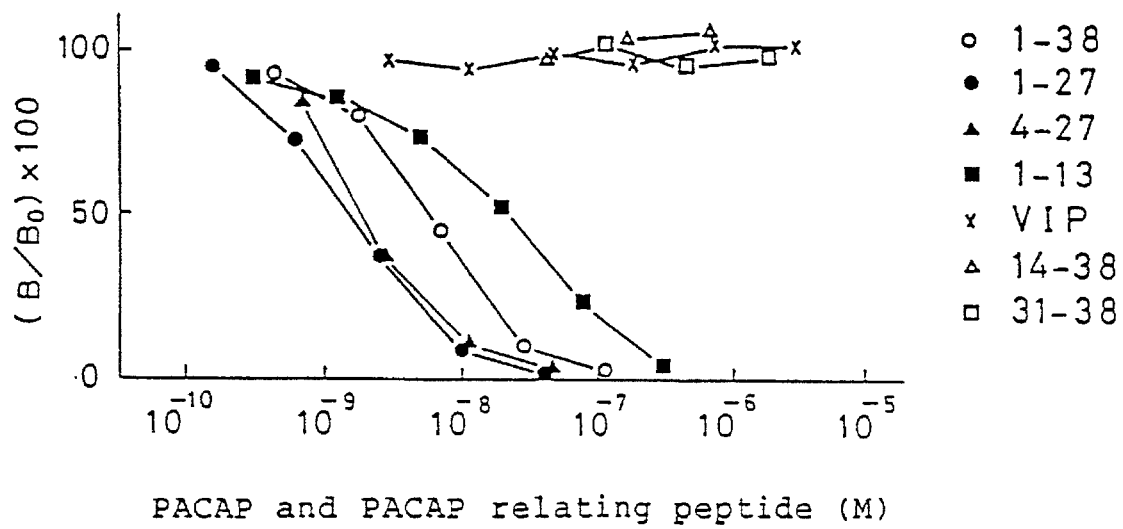
FIGS. 3(a)–(f) are a series of graphs showing the results assayed for PACAP38 and related peptides by a competitive method-enzyme immunoassay using antibodies of the present invention, thereby clarifying recognition sites of the antibodies of the present invention.

To the anti-mouse immunoglobulin antibody-bound microplate described in Example 5 were added 50 μl of a PA-1N culture supernatant diluted 50 times with buffer H and 50 μl of a buffer H solution of PACAP or a partial peptide of PACAP, such as PACAP38NH$_2$, PACAP27NH$_2$, PACAP(4–27), PACAP(1– 13), PACAP(14–38)NH$_2$, PACAP(31–38)NH$_2$ or VIP, followed by reaction at room temperature for 2 hours. Then, 50 μl of HRP-labeled PACAP38NH2 described in Example 4-1 (diluted 100 times with buffer H) was added thereto, followed by reaction at 4° C. for 16 hours. After reaction, the plate was washed with PBS, and then the enzyme activity on the solid phase was assayed by the method described in Example 5. The results are shown in FIG. 3(a). In the drawing, -o-, -●-, -▲-, -■-, -Δ-, -□- and -X- indicate PACAP38NH$_2$, PACAP27NH$_2$, PACAP(4–27)OH, PACAP(1–13)OH, PACAP(14–38)NH$_2$, PACAP(31–38)NH$_2$ and a standard curve of VIP, respectively.

As shown in FIG. 3(a), PA-1Na reacts with PACAP38NH$_2$, PACAP27NH$_2$, PACAP(1–13)OH and PACAP(4–27)OH, but does not react with PACAP(14–38)NH$_2$ and PACAP(31–38)NH$_2$. PA-1Na does not react with VIP either (the cross reactivity to PACAP38NH$_2$ is 0.1% or less). These results reveal that PA-1Na is an antibody belonging to class Ia which recognizes the N-terminal portion of PACAP38NH$_2$.

(2) Competitive Method-EIA Using PA-5Na

Figure 3B:
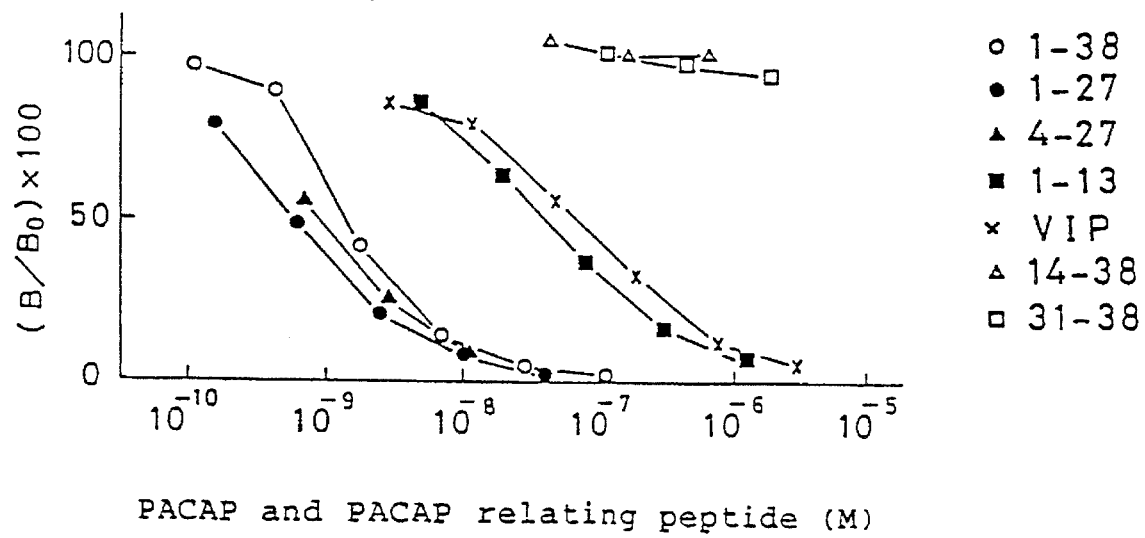
Figure 3C:
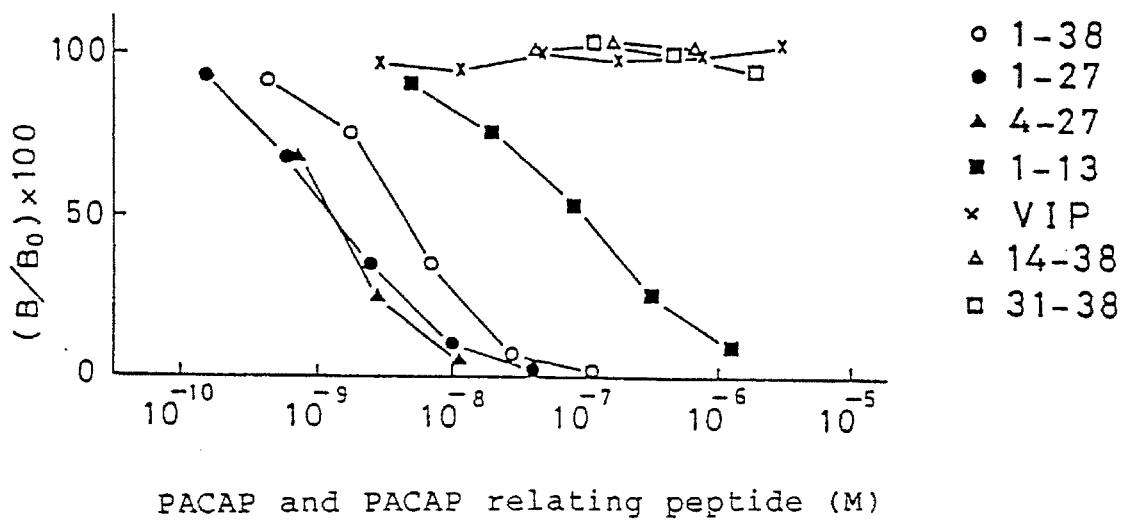

A competitive method-EIA using PA-5Na was carried out by the method described described in Example 14-(1). A culture supernatant of PA-5N was diluted 70 times. The results are shown in FIG. 3(c). PA-5Na reacts with PACAP38NH$_2$, PACAP27NH$_2$, PACAP(1–13)OH and PACAP(4–27)OH, but does not react with PACAP(14–38)NH$_2$ and PACAP(31–38)NH$_2$. PA-5Na does not react with VIP either (the cross reactivity is 0.1% or less). These results reveal that PA-5Na is an antibody belonging to class Ia which recognizes the N-terminal portion of PACAP38NH$_2$.

PA-1Na is different from PA-5Na in cross reactivity (to PACAP38NH$_2$) with PACAP(1–13)OH, and the cross reactivity of the former is at least 10 times stronger than that of the latter.

(3) Competitive Method-EIA Using PA-3Na

A competitive method-EIA using PA-3Na was carried out by the method described in Example 14-(1). A culture supernatant of PA-3N was diluted 50 times. The results are shown in FIG. 3(b). PA-3Na reacts with PACAP38NH$_2$, PACAP27NH$_2$, PACAP(1–13)OH and PACAP(4–27)OH, but does not react with PACAP(14–38)NH$_2$ and pacap(31–38)NH$_2$. On the other hand, PA-3Na shows a cross reactivity of 1% with VIP (to PACAP38NH$_2$). These results reveal that PA-5Na is an antibody belonging to class Ib which recognizes the N-terminal portion of PACAP38NH$_2$.

(4) Competitive Method-EIA Using PA-6Na

Figure 3D:
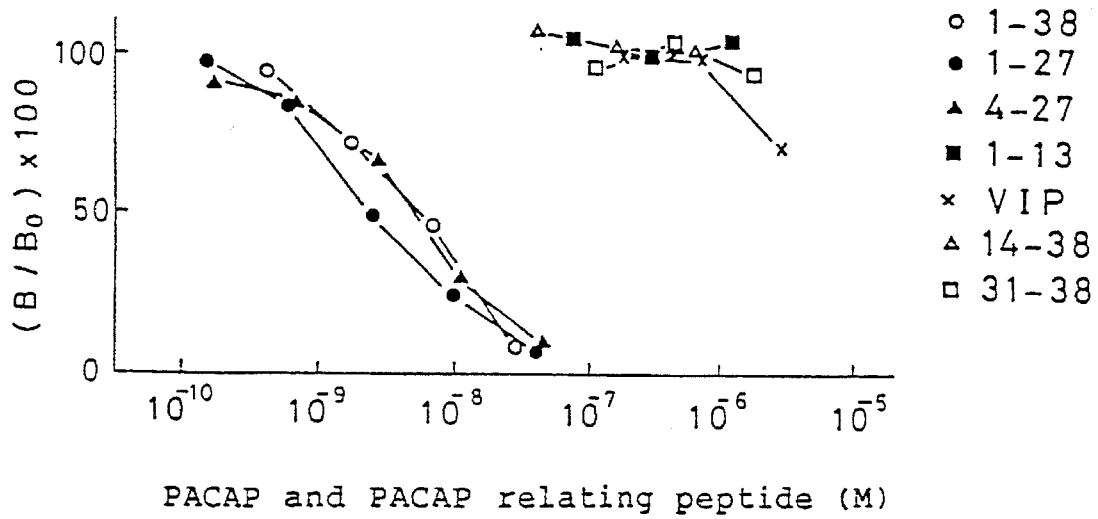

A competitive method-EIA using PA-6Na was carried out by the method described in Example 14-(1). A culture supernatant of PA-6N was diluted 40 times. The results are shown in FIG. 3(d). Pa-6Na reacts with PACAP38NH$_2$, PACAP27NH$_2$ and PACAP(4–27)OH, but does not react with PACAP(1–13)OH, PACAP(14–38)NH$_2$ and PACAP(31–38)NH$_2$. PA-6Na does not react with VIP either (the cross reactivity to PACAP38NH$_2$ is 0.1% or less). These results reveal that PA-6Na is an antibody belonging to class II which recognizes the region from the N-terminal portion to the central portion of PACAP38NH$_2$.

(5) Competitive Method-EIA Using PA-2Ca

Figure 3E:
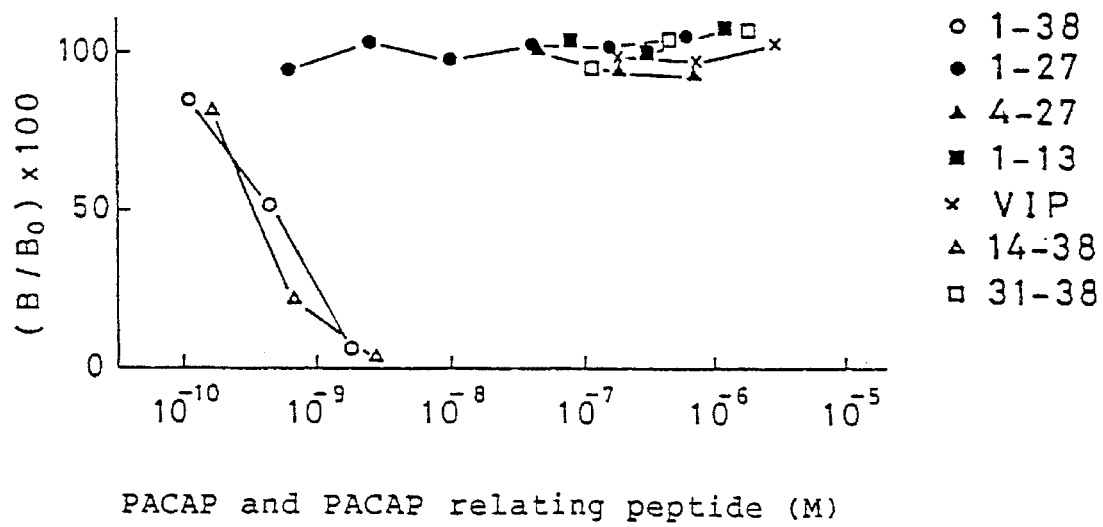

A competitive method-EIA using PA-2Ca was carried out by the method described in Example 14-(1). A culture supernatant of PA-2C was diluted 340 times. The results are shown in FIG. 3(e). PA-1Ca reacts with PACAP38NH$_2$ and PACAP(14–38)NH$_2$, but does not react with PACAP27NH$_2$, PACAP(4–27)OH PACAP(1–13)OH and PACAP(31–38)NH$_2$. PA-2Ca does not react with VIP either (the cross reactivity to PACAP38NH$_2$ is 0.1% or less). These results reveal that PA-2Ca is an antibody belonging to class III which recognizes the region from the C-terminal portion to the central portion of PACAP38NH$_2$.

(6) Competitive Method-EIA Using PA-1Ca

Figure 3F:
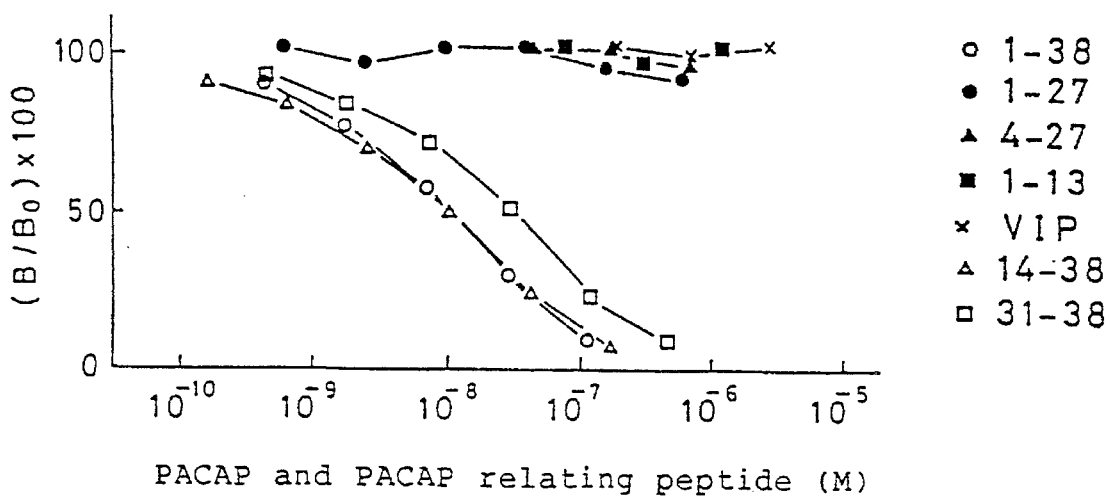

A competitive method-EIA using PA-1Ca was carried out by the method described in Example 14-(1). A culture supernatant of PA-1C was diluted 35 times. The results are shown in FIG. 3(f). PA-1Ca reacts with PACAP38NH$_2$, PACAP(14–38)NH$_2$ AND pacap(31–38)NH$_2$, but does not react with PACAP27NH$_2$, PACAP(4–27)OH and PACAP(1–13)OH. PA-6Na does not react with VIP either (the cross reactivity to PACAP38NH$_2$ is 0.1% or less). These results reveal that PA-2Ca is an antibody belonging to class IV which recognizes the C-terminal portion of PACAP38NH$_2$.

At least 400, 100, 200, 200, 20 or 200 pg/well (a PACAP concentration giving B/BO=80%) of PACAP38NH$_2$ could be detected by the competitive method EIA using PA-1Na, PA-5Na, PA-3Na, PA-6Na, PA-2Ca or PA-1Ca.

EXAMPLE 15

Sandwich Method-EIA

(1) Sandwich Method-EIA Using PA-6Na F(ab')$_2$-HRP

Into each well of a 96-well microplate was poured 100 µl of 0.1M carbonate buffer (pH 9.6) containing 15 µg/ml of purified monoclonal antibody PA-1Na, PA-3Na, PA-5Na, PA-6Na, PA-2Ca or PA-1Ca described in Example 10, and the plate was allowed to stand at 4° C. for 24 hours. The excess binding sites of the wells were inactivated by adding 300 µl of Blockace diluted 4 times with PBS.

Figure 4:
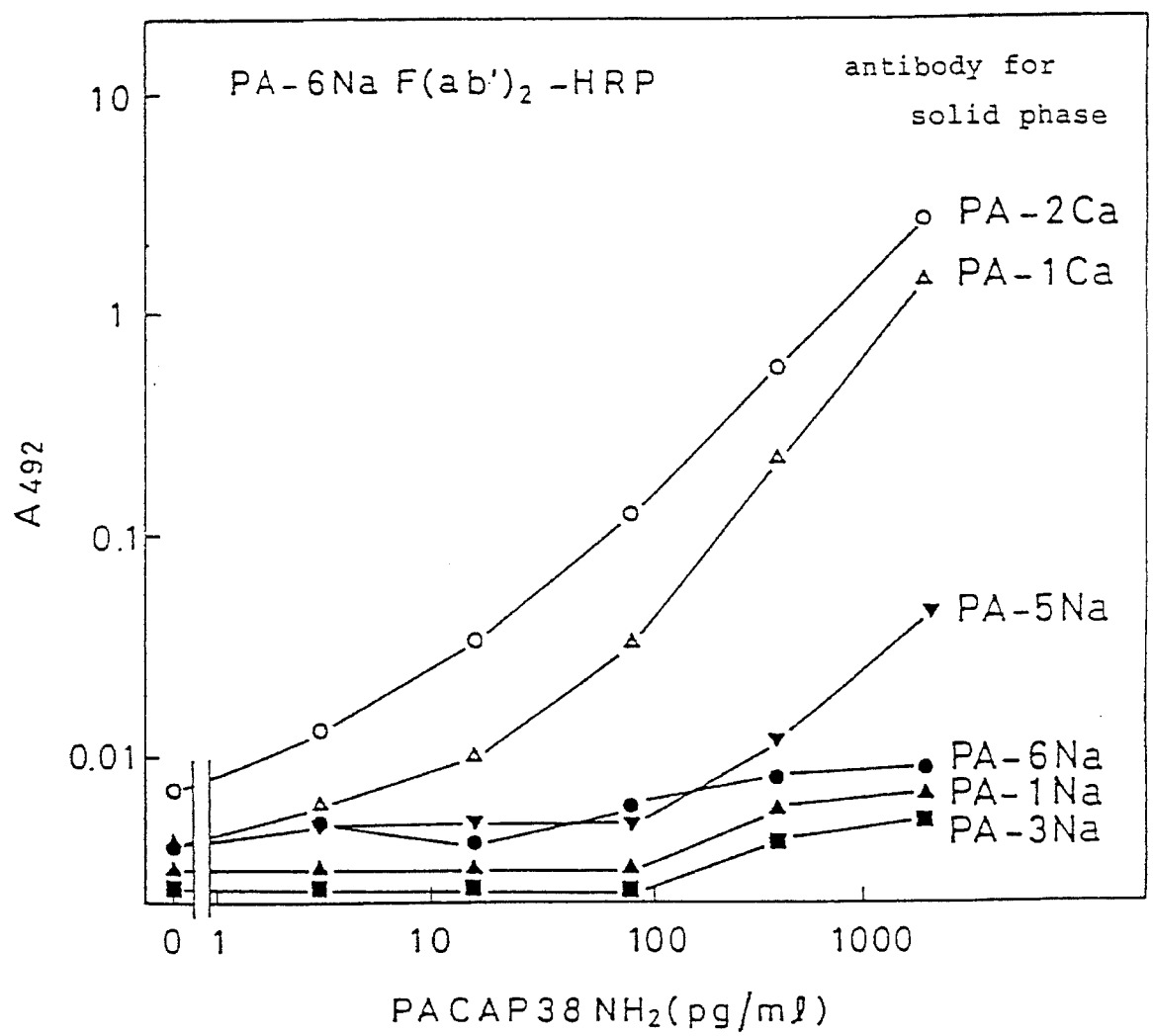
FIGS. 4 to 6 are graphs showing the results detected for PACAP38NH$_2$ by sandwich method-enzyme immunoassays using antibodies of the present invention.

To each well of the plate thus prepared was added 100 µl of a standard solution of PACAP38NH$_2$ diluted with buffer E, followed by reaction at 4° C. for 24 hours. After washing with PBS, 100 µl of HRP-labeled PA-γNa F(ab')$_2$ prepared in Example 13-(1) described above (diluted 100 times with buffer C) was added thereto, followed by reaction at 4° C. for 24 hours. After washing with PBS, the enzyme activity on the solid phase was assayed by the method described in Example 5. The results are shown in FIG. 4.

In the sandwich method-EIA using PA-6Na (class II) F(ab')$_2$-HRP, the sensitivity was highest when PA-2Ca (class III) was used as the antibody for solid phase, and at least 0.4 pg/well of PACAP38NH$_2$ could be detected. When PA-1Ca (class IV) was used as the antibody for solid phase, 2 pg/well of PACAP38NH$_2$ could be detected, and when PA-5Na (class Ia) was used, 40 pg/well of PACAP38NH$_2$ could be detected.

The above results reveal that when PA-6Na, an antibody of class II, is used as a marker, the sandwich-EIA can be established even if an antibody of any other class (including a class adjacent thereto in primary arrangement) is used as the antibody for solid phase, and particularly that the sandwich method-EIA using PA-2Ca, an antibody of class III, as the antibody for solid phase is highly sensitive.

(2) Sandwich Method-EIA Using PA-1Ca F(ab')$_2$-HRP

Figure 5:
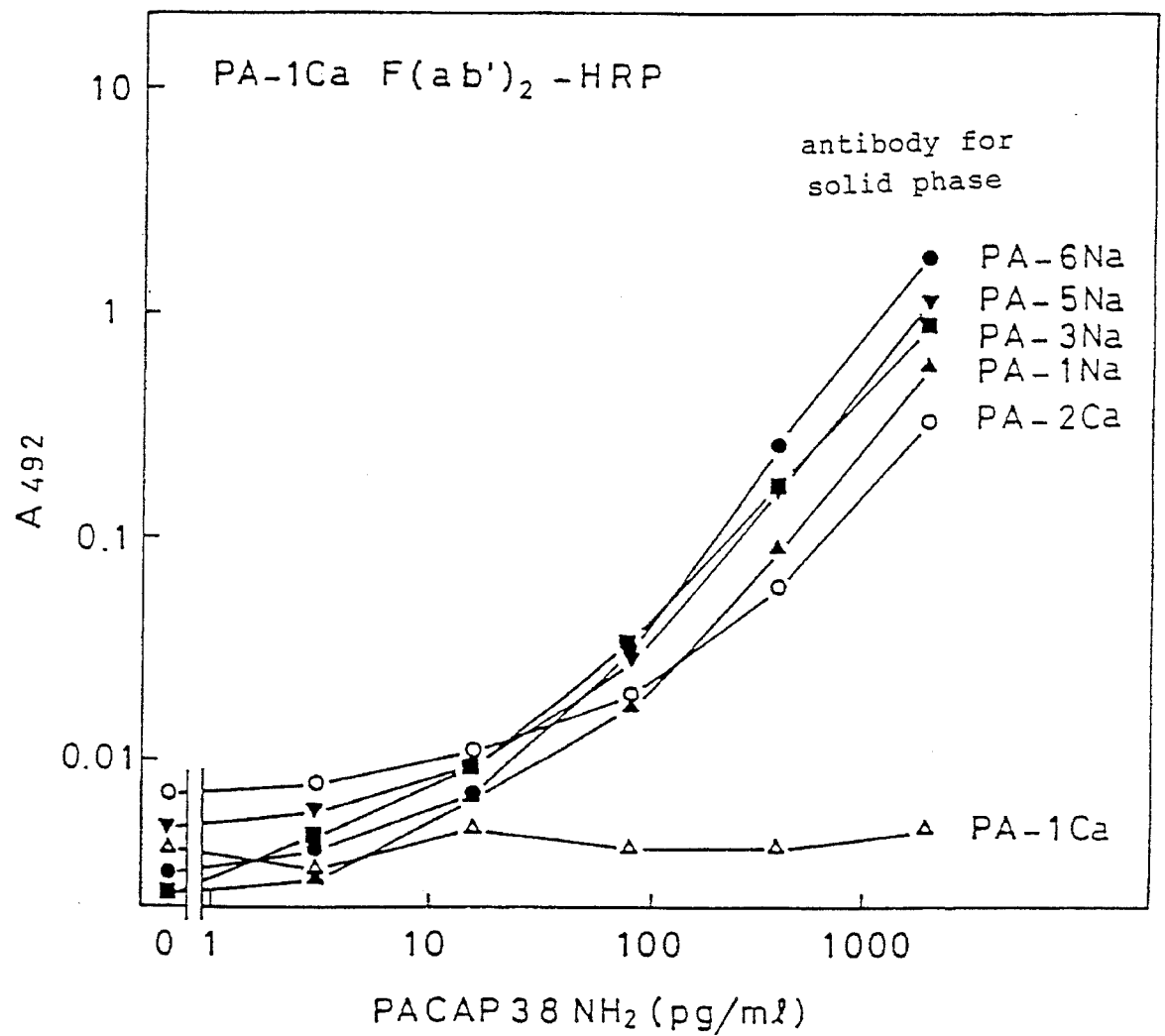

A sandwich method-EIA using a microplate sensitized with each of various antibodies described in the above item (1) and HRP-labeled PA-1Ca F(ab')$_2$ described in Example 13-(2) was carried out by the method described in the above item (1). The results are shown in FIG. 5.

In the sandwich method-EIA using PA-1Ca (class IV) F(ab')$_2$-HRP, the sensitivity was highest when PA-3Na (class Ib) was used as the antibody for solid phase, and at least 1 pg/well of PACAP38NH$_2$ could be detected. When PA-1Na (class Ia), PA-5Na (class Ia) or PA-6Na (class II) was used as the antibody for solid phase, at least 2 pg/well of PACAP38NH$_2$ could be detected. Further, even when and antibody of class III adjacent in primary arrangement was used, at least 8 pg/well of PACAP38NH$_2$ was detected.

The above results reveal that when PA-1Ca, an antibody of class IV, is used as a marker, the sandwich-EIA can be established even if an antibody of any other class (including a class adjacent thereto in primary arrangement) is used as the antibody for solid phase, and particularly that the sandwich method-EIA using PA-3Na, an antibody of class Ib, as the antibody for solid phase is highly sensitive.

(3) Sandwich Method-EIA Using PA-2Ca IgG-HRP

Figure 6:
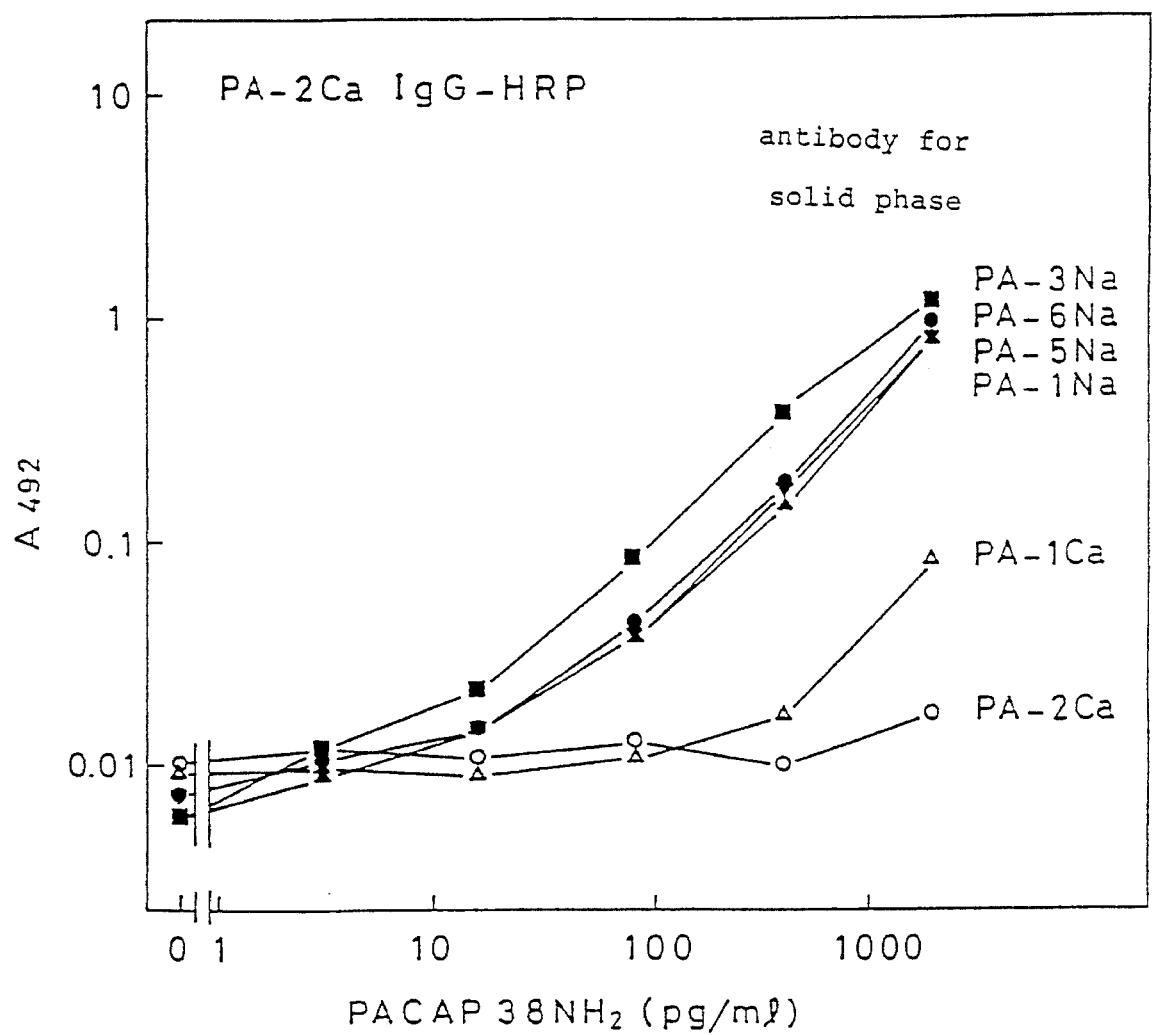

A sandwich method-EIA using a microplate sensitized with each of various antibodies described in the above item (1) and HRP-labeled PA-2Ca IgG described in Example 13-(3) was carried out by the method described in the above item (1). The results are shown in FIG. 6.

In the sandwich method-EIA using PA-2Ca (class III) IgG-HRP, the sensitivity was highest when PA-3Na (class Ib) was used as the antibody for solid phase, and at least 2 pg/well of PACAP38NH$_2$ could be detected. When PA-1Na, PA-5Na or PA-6Na was used as the antibody for solid phase, 4 pg/well of PACAP38NH$_2$ was detected, and when PA-1Ca was used, 80 pg/well of PACAP38NH$_2$ was detected.

The above results reveal that when PA-2Ca, an antibody of class III, is used as a marker, the sandwich-EIA can be established even if an antibody of any other class (including a class adjacent thereto in primary arrangement) is used as the antibody for solid phase, and particularly that the sandwich method-EIA using PA-3Na, an antibody of class Ib, as the antibody for solid phase in highly sensitive.

EXAMPLE 16

Specificity of Sandwich Method-EIA

Figure 7:
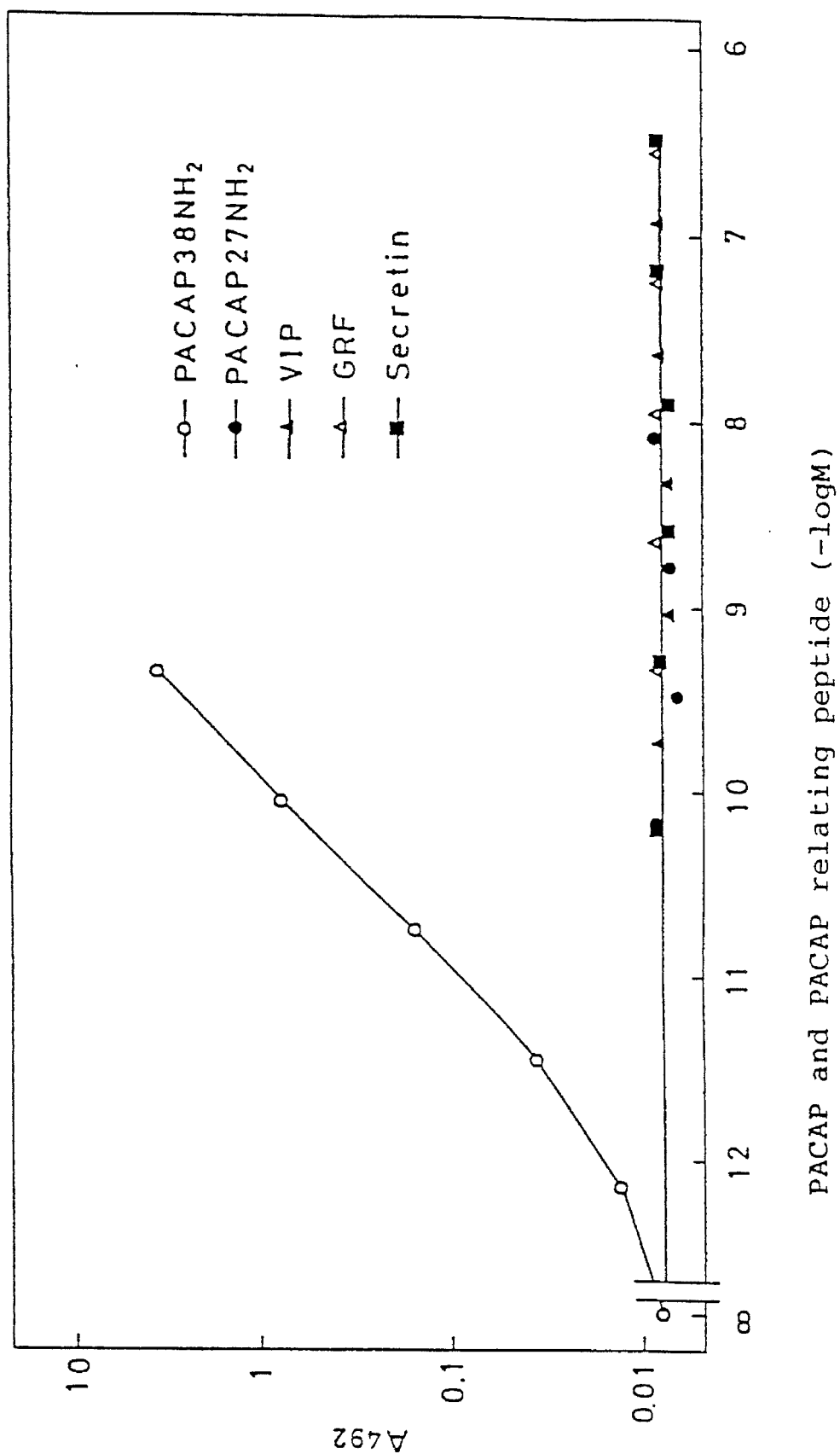
FIG. 7 is a graph showing the reactivity of PACAP and related peptides in the sandwich method-enzyme immunoassay of the present invention.

In a sandwich method-EIA using PA-2Ca described in Example 15-(1) as the antibody for solid phase and PA-6Na F(ab')$_2$-HRP as the antibody for labeling, the reactivity to PACAP38NH$_2$, VIP GRF and secretin was examined. The results are shown in FIG. 7.

In the drawing, -o-, -●-, -▲-, -△- and -■- indicate concentration-dependent curves of PACAP38NH$_2$, PACAP27NH$_2$, VIP, GRF and secretin, respectively.

In the above assay, the cross reactivity to all of PACAP27NH$_2$, VIP, GRF and secretin is 0.001%. This reveals that the above assay is specific for PACAP38NH$_2$.

EXAMPLE 17

Purification of Rabbit PACAP(11–27)NH$_2$ Antibody

An affinity solid phase for purifying rabbit PACAP(11–27)NH$_2$ was prepared. Namely, 4.5 mg of [Cys$^{10}$]PACAP(11–27)NH$_2$ was dissolved in 20 ml of 0.1M sodium hydrogencarbonate containing 0.5M NaCl, and reacted with 3 g of CNBr-activated Sepharose 4B at room temperature for 3 hours. Then, after unreacted active groups were treated with 0.1M Tris-hydrochloric acid buffer (pH 8), the resulting product was dispersed in PBS and charged into a column.

8 ml of rabbit PACAP(11–27)NH$_2$ antiserum 1C, 8 ml of 2C and 16 ml of 3C in which high antibody activity was observed (see FIG. 2) were mixed with one another, and 32 ml of PBS was added thereto. Then, 52 ml of saturated ammonium sulfate was slowly added thereto with stirring, followed by centrifugation at 12,000×g for 20 minutes. The precipitate was dissolved in 25 ml of borate buffer (pH 8) containing 0.15M NaCl (BBS), followed by dialysis against BBS at 4° C. for 2 days. After dialysis, the resulting solution was loaded on the above-mentioned column and thoroughly washed with BBS. Then, specific antibodies were eluted with 0.1M acetate buffer (pH 4.5) containing 0.5M NaCl and further with 0.05M glycine-hydrochloric acid buffer (pH 2.0) containing 0.1M NaCl. As a result, 5.4 mg and 6.7 mg of the specific antibodies were obtained in fractions eluted at pH 4 and pH 2, respectively.

EXAMPLE 18

Preparation of Anti-PACAP(11–27)NH$_2$ Fab'-HRP

An Fab'-peroxidase marker was prepared from the anti-PACAP(11–27)NH$_2$ antibody described in Example 17 according to the method of Ishikawa et al. [*J. Appl. Biochem.* 6, 56–63 (1984)].

Namely, 5.6 mg of the specific antibody was dissolved in 0.1M acetate buffer (pH 4.5), and 160 µg of pepsin (crystallized twice, Sigma) was added thereto, followed by reaction at 37° C. for 20 hours. Then, the reaction product was subjected to an FPLC (Pharmacia) using a Superose 12 column equilibrated with 0.1M acetate buffer (pH 5) to obtain 2.2 mg of an F(ab')$_2$ fraction. β-Mercaptoethylamine was added to this fraction to a final concentration of 20 mM, and the resulting solution was allowed to stand at 37° C. for 90 minutes. Then, the reaction solution was separated on a Sephadex G-25 Column equilibrated with 0.1M phosphate buffer (pH 6.0) containing 5 mM EDTA to obtain an Fab' fraction.

On the other hand, 6 mg of maleimidated HRP prepared according to the method described in Example 4-2 and the total amount of the above-mentioned anti-PACAP(11–27)NH Fab' fraction were mixed and reacted with each other at 4° C. for 1 days. Then, the reaction product was fractionated on an Ultrogel AcA44 column equilibrated with 0.1M phosphate buffer to purify HRP-labeled anti-PACAP(11–27)NH$_2$ Fab'.

EXAMPLE 19

Figure 8:
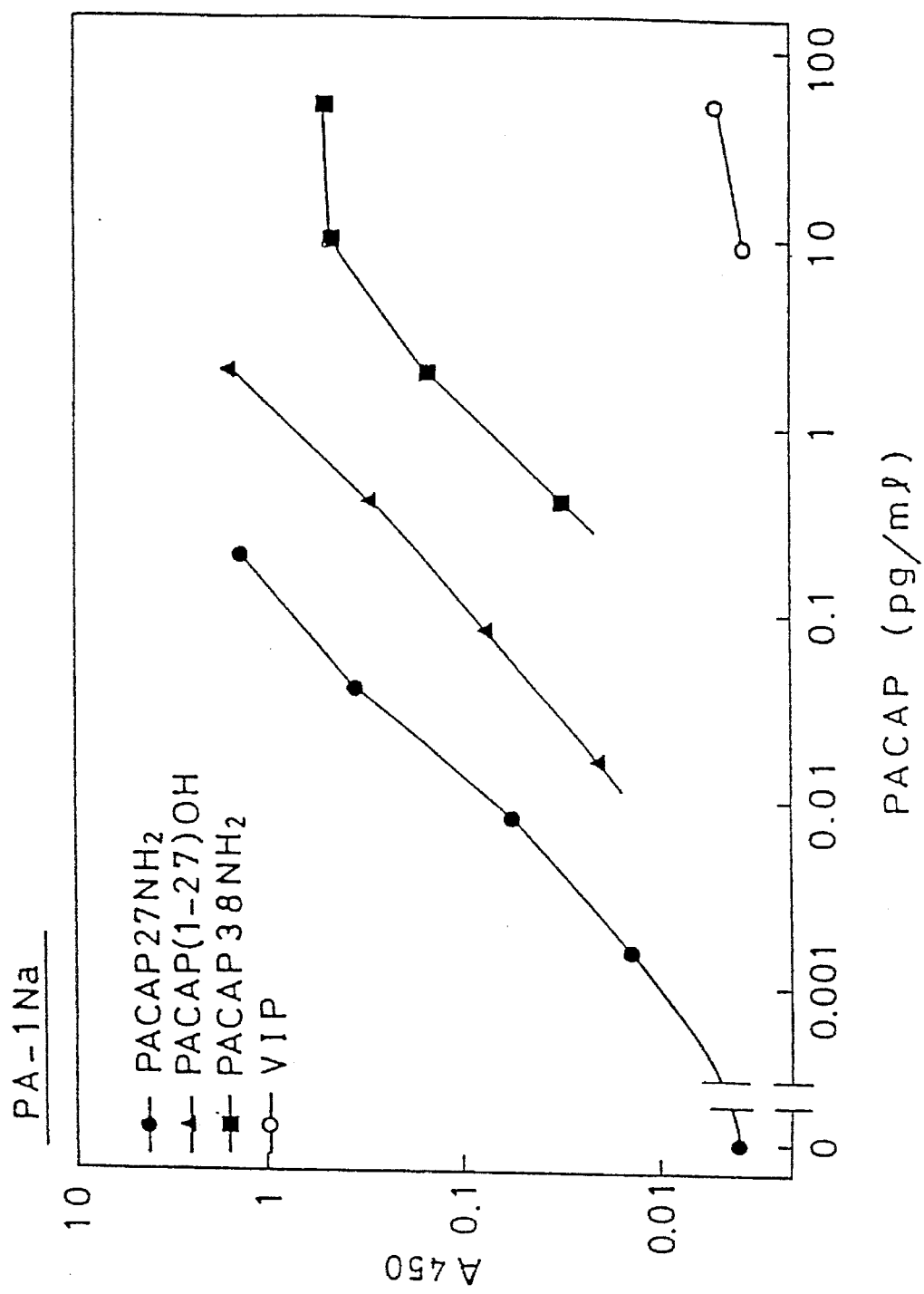
FIGS. 8 to 11 are graphs showing the reactivity of PACAP27NH$_2$ and related peptides in the sandwich method-enzyme immunoassays.

Sandwich Method-EIA for Assaying PACAP27NH$_2$ (1) To a microplate on which PA-1Na described in Example 15 was fixed, 100 µl of a standard solution of PACAP27NH$_2$, PACAP(11–27)OH or PACAP38NH$_2$ was added, followed by reaction at 4° C. for 24 hours. After washing with PBS, HRP-labeled anti-PACAP(11–27)NH$_2$ Fab' described in Example 18 (diluted 400 times with buffer C) was added thereto and reacted at 4° C. for 24 hours. After washing with PBS, the enzyme activity on the solid phase was assayed by the method described in Example 5-2. The results are shown in FIG. 8.

In the drawing, -●-, -▲-, -■- and -o- indicate PACAP27NH$_2$, PACAP(11–27)OH, PACAP38NH$_2$ and VIP, respectively. The results shown in FIG. 8 reveal that 0.2 pg/well of PACAP27NH$_2$ can be detected by this assay with a cross reactivity of 11.5% with PACAP(11–27)OH and with a cross reactivity of 0.97% by weight ratio or 1.3% by mole ratio with PACAP38NH$_2$.

Figure 9:
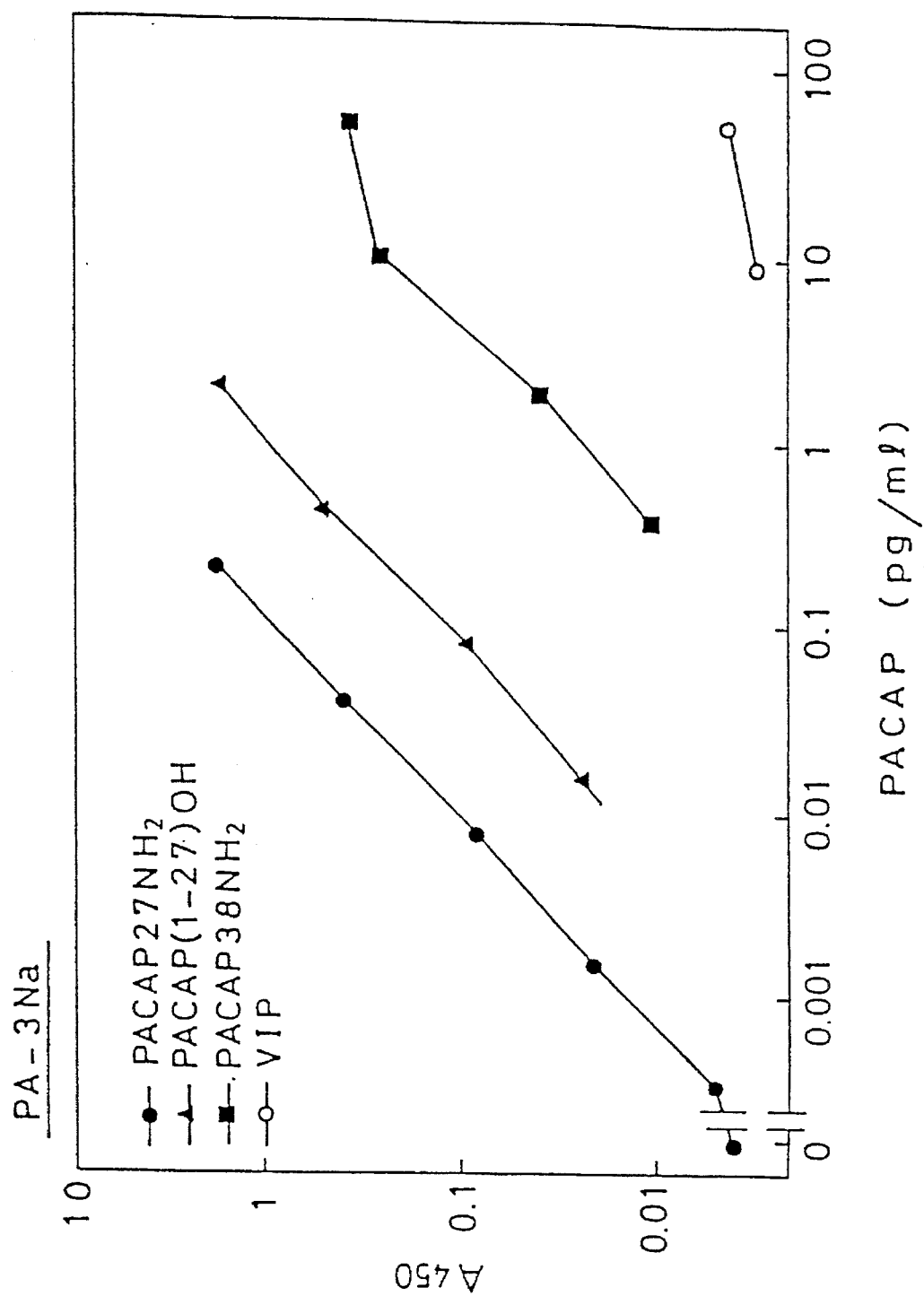

(2) Using a microplate on which PA-3Na described in Example 15 was fixed and HRP-labeled PACAP(11–27)NH$_2$ Fab' described in Example 18, a sandwich method-EIA was carried out by the method described above. The results are shown in FIG. 9. These results reveal that 0.2 pg/well of PACAP27NH$_2$ can be detected by this assay with a cross reactivity of 11% with PACAP(11–27)OH and with a cross reactivity of 0.22% by weight ratio or 0.31% by mole ratio with PACAP38NH$_2$.

Figure 10:
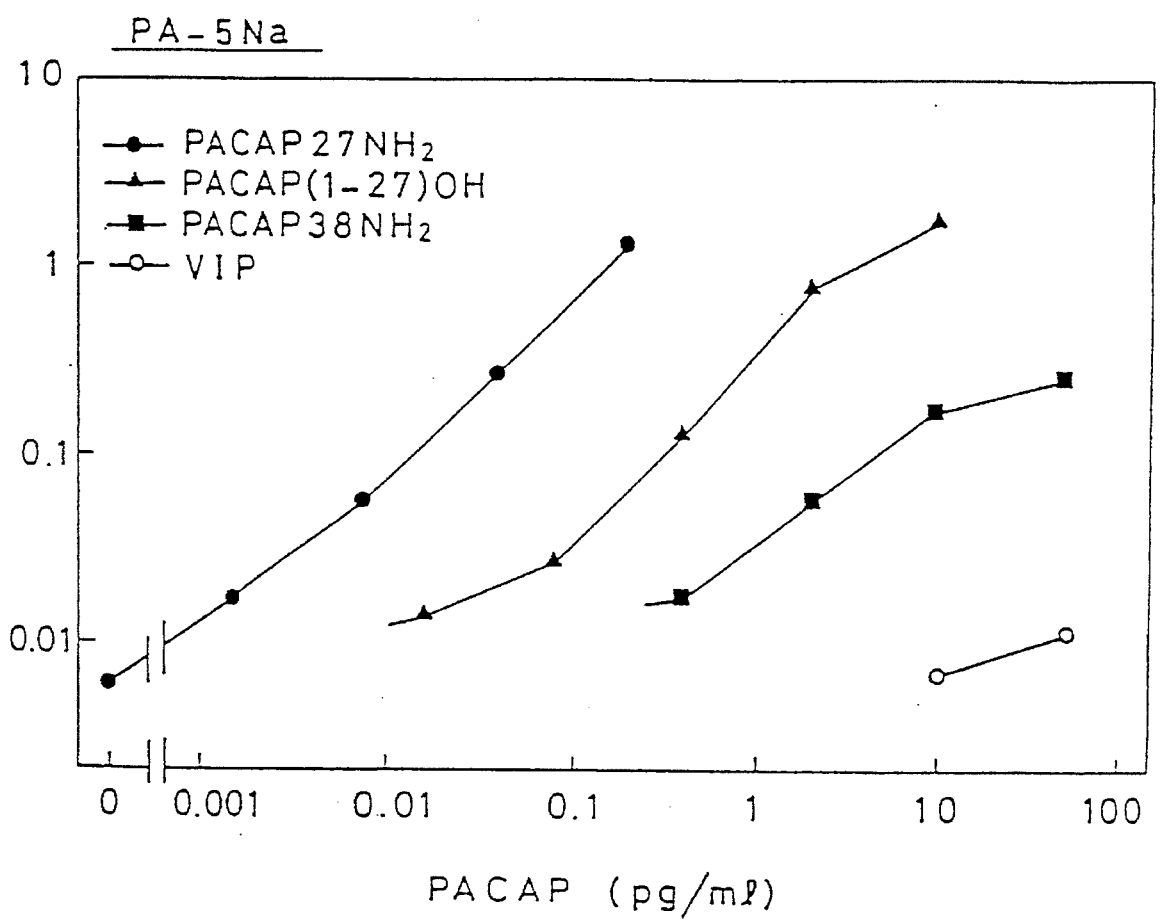

(3) Using a microplate on which PA-5Na described in Example 15 was fixed and HRP-labeled PACAP(11–27)NH$_2$ Fab' described in Example 18, a sandwich method-EIA was carried out by the method described above. The results are shown in FIG. 10. These results reveal that 0.2 pg/well of PACAP27NH$_2$ can be detected by this assay with a cross reactivity of 4.1% with PACAP(11–27)OH and with a cross reactivity of 0.40% by weight ratio or 0.56% by mole ratio with PACAP38NH$_2$.

Figure 11:
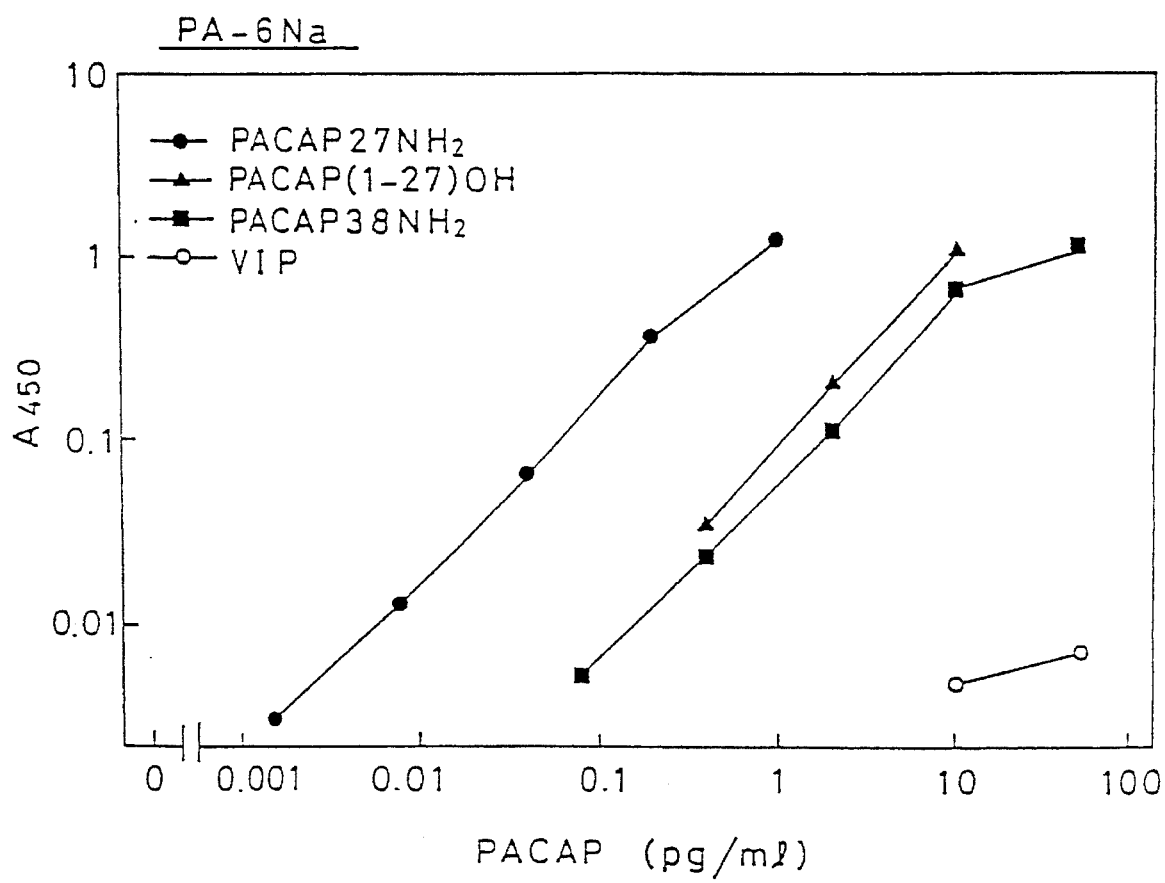

(4) Using a microplate on which PA-6Na described in Example 15 was fixed and HRP-labeled PACAP(11–27)NH$_2$ Fab' described in Example 18, a sandwich method-EIA was carried out by the method described above. The results are shown in FIG. 11. These results reveal that 0.8 pg/well of PACAP27NH$_2$ can be detected by this assay with a cross reactivity of 5.4% with PACAP(11–27)OH and with a cross reactivity of 3.6% by weight ratio or 5.00% by mole ratio with PACAP38NH$_2$.

All of the assays only exhibited a cross reactivity of 0.001% or less with VIP.

From the above results, PACAP27NH$_2$ can be detected by the use of these assays with a cross reactivity of 0.22 to 3.6% by weight ratio or with a cross reactivity of 0.31 to 5.0% by mole ratio with PACAP38NH$_2$. It is therefore possible to fractionate and determine PACAP27NH$_2$ and PACAP38NH$_2$ by combinations of these assays and the assay described in Example 16.

EXAMPLE 20

Examination of Neutralization Activity of Anti-PACAP Antibodies

Figure 12:
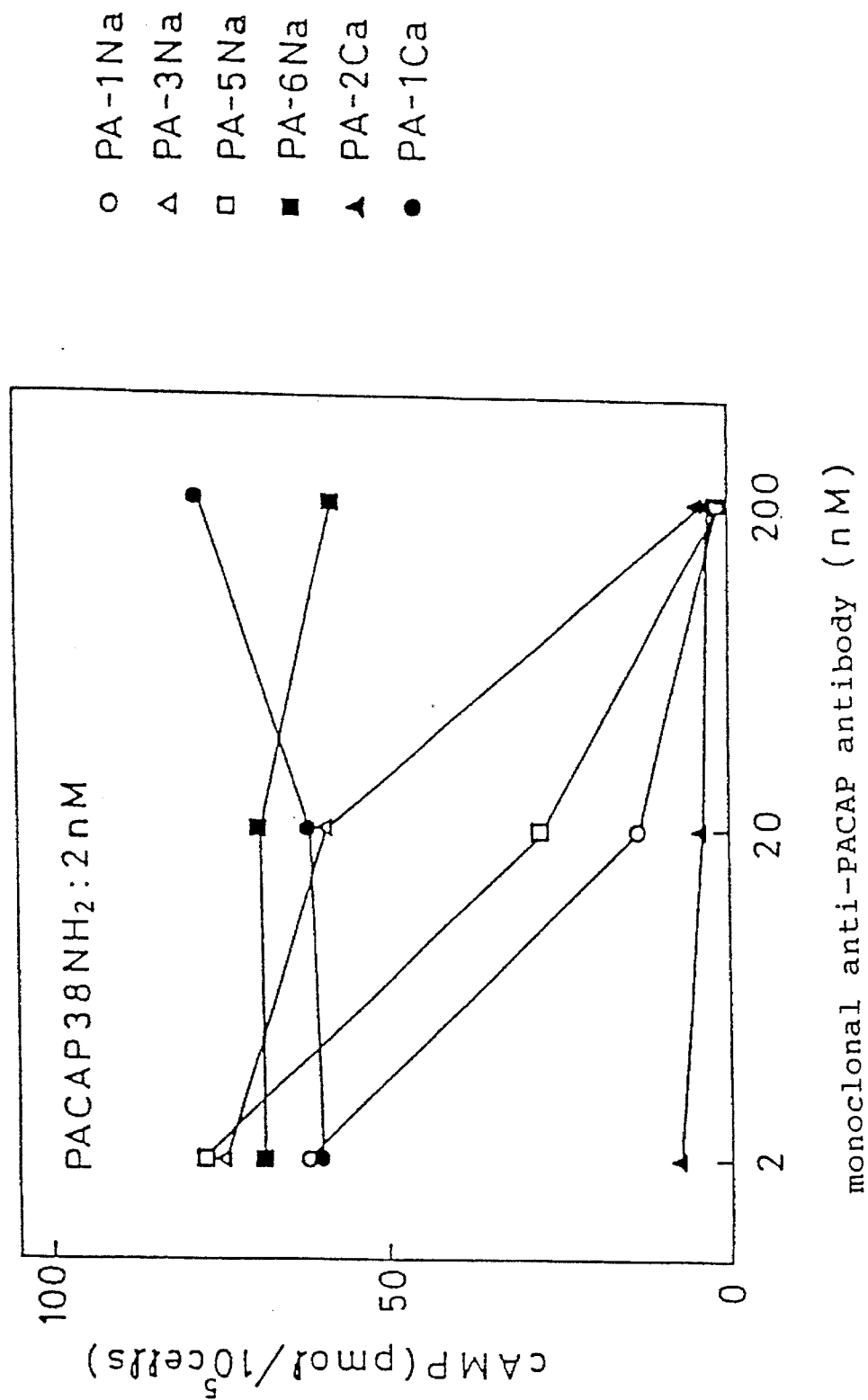
FIG. 12 is a graph showing the results of examination of the neutralization activity of anti-PACAP antibodies to PACAP38NH$_2$ by the use of cultured cells.
Figure 13:
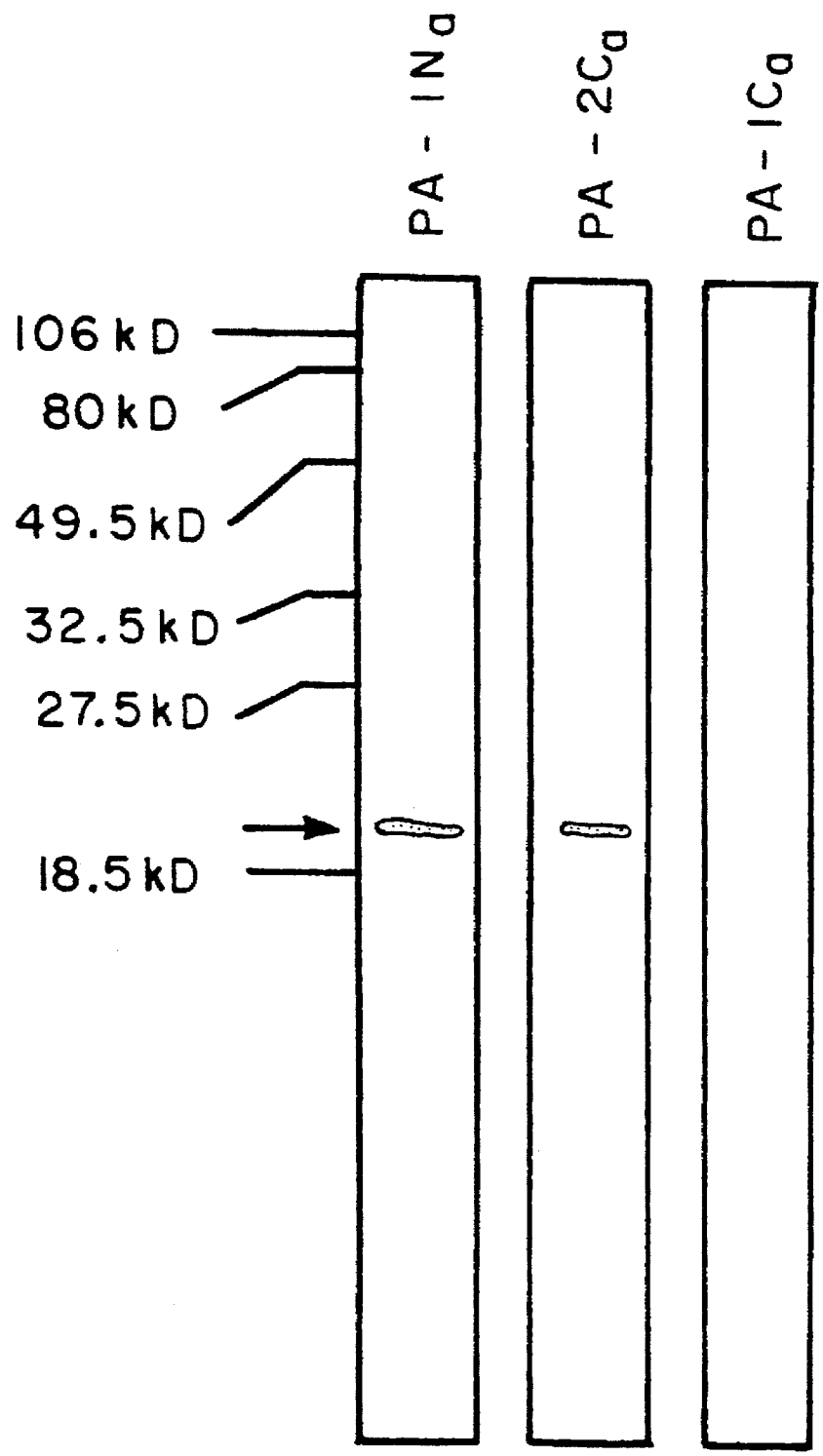
FIG. 13 shows immunoblot analysis of the products of *E. coli* transfected with the expression plasmid containing human prepro-PACAP cDNA.

Rat adrenal brown cytoma strain PC-12h (supplied by Dr. Hatanaka, Protein Laboratory, Osaka University) was disseminated at a rate of 5×10$^4$ cells/well on a 48-well multi-well plate (Sumitomo Bakelite) treated with collagen, and incubated in Dulbecco's modified Eagle's medium (DMEM) containing 10% FCS for 7 to 10 days. The medium of the plate was exchanged with Hnak's balanced salt solution (HBSS) containing 0.05% BSA, followed by incubation for 30 minutes. Then, PACAP38NH$_2$ (final concentration: 2 nM) was added thereto which had previously been reacted with each of the anti-PACAP antibodies (final concentration: 2, 20 or 200 nM) at 4° C. for 1 hour. After additional incubation for 2 hours, the concentration of cAMP contained in the culture supernatant was measured with a cAMP measuring kit (Amersham). The results are shown in FIG. 12. In the drawing, -o-, -Δ-, -□-, -■-, ▲- and -●- indicate PA-1Na, PA-3Na, PA-5Na, PA-6Na, PA-2Ca and PA-1Ca, respectively. These results reveal that four kinds of these six kinds of monoclonal anti-PACAP antibodies have neutralization activity to PACAP38NH$_2$ and the order of its strength is PA-2Ca (an antibody of class III)>PA-1Na (an antibody of class Ia)>PA-5Na (an antibody of class Ia)>PA-3Na (an antibody of class Ib).

The use of the various monoclonal antibodies of the present invention which recognized the continuous sites in primary arrangement of PACAP revealed immunochemical properties of PACAP. By using these antibodies, it is possible to establish assay systems using various competitive or sandwich methods different in specificity for PACAP or its related peptides. In particular, it becomes possible to fractionate and determine PACAP38NH$_2$ and PACAP27NH$_2$ with high sensitivity by combinations of various sandwich methods.

EXAMPLE 21

Examination of Reactivity of Anti-PACAP Monoclonal Antibodies with Human PACAP Precursor

*Escherichia coli* cells having plasmid pTS401 in which human PACAP precursor genes were integrated were cultivated in 10 ml of M9 medium (containing 0.1% NZ amine, 0.4% glucose, 50 μg/ml ampicillin and 25 μg/ml chloramphenicol) at 37° C. When the cells were proliferated to have an absorbance of 0.7 at 600 nm, isopropyl-β-D-thiogalactopyranoside was added thereto, and cultivation was further continued for 3 hours, followed by centrifugation at 5,000 g for 10 minutes to collect the cells. As a control, the cells were collected just before addition of isopropyl-β-D-thiogalactopyranoside.

To the cells, 1 ml of SDS-containing sample buffer of Laemmli was added, and the mixture was boiled at 100° C. for 5 minutes, followed by electrophoresis on 16% polyacrylamide gel. The protein was electrically transferred to nitrocellulose filters by the western blotting method, and each of anti-PACAP mouse monoclonal antibodies PA-1Na, PA-1Ca and PA-2Ca was reacted with the protein on each filter. Then, the secondary antibody (anti-mouse IgG-peroxidase, Cappel.) was reacted therewith. The band of the desired protein was stained and fixed by a POD immunostain set (Wako Pure Chemical Industries). The bands reacting with anti-PACAP mouse monoclonal antibodies PA-1Na and PA-2Ca were observed in the vicienity of a molecularf weight of about 18,000 daltons. The bands approximately agree with molecular weight of human PACAP precursor deduced from cDNA coding for human PACAP. This fact reveals that anti-PACAP mouse monoclonal antibodies PA-1Na and PA-2Ca react with human PACAP precursor.

---

What is claimed is:
1. The hybridoma cell line FERM BP-2811.
2. The hybridoma cell line FERM BP-2813.
3. The hybridoma cell line FERM BP-2814.
4. The hybridoma cell line FERM BP-2815.
5. The hybridoma cell line FERM BP-2816.
6. Monoclonal antibody PA-1Na, produced by the hybridoma cell line of claim 1.
7. Monoclonal antibody PA-5Na, produced by the hybridoma cell line of claim 2.
8. Monoclonal antibody PA-6Na, produced by the hybridoma cell line of claim 3.
9. Monoclonal antibody PA-2Ca, produced by the hybridoma cell line of claim 4.
10. Monoclonal antibody PA-1Ca, produced by the hybridoma cell line of claim 5.
11. A polyclonal antibody which specifically binds to a C-terminal peptide of PACAP27 represented by SEQ ID NO:7.

* * * * *

UNITED STATES PATENT AND TRADEMARK OFFICE
CERTIFICATE OF CORRECTION

PATENT NO. : 5,486,472
DATED : Jan. 23, 1996
INVENTOR(S) : Suzuki, et al

It is certified that error appears in the above-indentified patent and that said Letters Patent is hereby corrected as shown below:

On title page, item [30] replace "Mar. 17, 1990 [JP] Japan...2-5565" with --Mar. 17, 1990 [JP] Japan...2-65565--

Signed and Sealed this

Eighteenth Day of June, 1996

*Attest:*

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
His  Ser  Asp  Gly  Ile  Phe  Thr  Asp  Ser  Tyr  Ser  Arg  Tyr  Arg  Lys  Gln
1                   5                        10                       15

Met  Ala  Val  Lys  Lys  Tyr  Leu  Ala  Ala  Val  Leu  Gly  Lys  Arg  Tyr  Lys
```

20                          25                          30

Gln Arg Val Lys Asn Lys
                    35

(2) INFORMATION FOR SEQ ID NO:2:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:2:

His Ser Asp Gly Ile Phe Thr Asp Ser Tyr Ser Arg Tyr Arg Lys Gln
        1               5                   10                  15

Met Ala Val Lys Lys Tyr Leu Ala Ala Val Leu
                        20                  25

(2) INFORMATION FOR SEQ ID NO:3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:3:

His Ser Asp Gly Ile Phe Thr Asp Ser Tyr Ser Arg Tyr
        1               5                   10

(2) INFORMATION FOR SEQ ID NO:4:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:4:

Gly Ile Phe Thr Asp Ser Tyr Ser Arg Tyr Arg Lys Gln Met Ala Val
        1               5                   10                  15

Lys Lys Tyr Leu Ala Ala Val Leu
                        20

(2) INFORMATION FOR SEQ ID NO:5:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:5:

Arg Lys Gln Met Ala Val Lys Lys Tyr Leu Ala Ala Val Leu Gly Lys
        1               5                   10                  15

Arg Tyr Lys Gln Arg Val Lys Asn Lys
                        20                  25

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear ( i i ) MOLECULE TYPE: peptide ( x i ) SEQUENCE DESCRIPTION: SEQ ID NO:6:

```
Tyr  Lys  Gln  Arg  Val  Lys  Asn  Lys
 1              5
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ser  Arg  Tyr  Arg  Lys  Gln  Met  Ala  Val  Lys  Lys  Tyr  Leu  Ala  Ala  Val
 1              5                        10                       15
Leu
```

( 2 ) INFORMATION FOR SEQ ID NO:8:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Thr  Met  Cys  Ser  Gly  Ala  Arg  Leu  Ala  Leu  Leu  Val  Tyr  Gly  Ile
 1              5                        10                       15

Ile  Met  His  Ser  Ser  Val  Tyr  Ser  Ser  Pro  Ala  Ala  Ala  Gly  Leu  Arg
              20                        25                       30

Phe  Pro  Gly  Ile  Arg  Pro  Glu  Glu  Ala  Tyr  Gly  Glu  Asp  Gly  Asn
          35                        40                       45

Pro  Leu  Pro  Asp  Phe  Gly  Gly  Ser  Glu  Pro  Pro  Gly  Ala  Gly  Ser  Pro
     50                        55                       60

Ala  Ser  Ala  Pro  Arg  Ala  Ala  Ala  Ala  Trp  Tyr  Arg  Pro  Ala  Gly  Arg
65                       70                        75                      80

Arg  Asp  Val  Ala  His  Gly  Ile  Leu  Asn  Glu  Ala  Tyr  Arg  Lys  Val  Leu
                    85                        90                       95

Asp  Gln  Leu  Ser  Ala  Gly  Lys  His  Leu  Gln  Ser  Leu  Val  Ala  Arg  Gly
               100                       105                      110

Val  Gly  Gly  Ser  Leu  Gly  Gly  Gly  Ala  Gly  Asp  Asp  Ala  Glu  Pro  Leu
          115                       120                      125

Ser  Lys  Arg  His  Ser  Asp  Gly  Ile  Phe  Thr  Asp  Ser  Tyr  Ser  Arg  Tyr
     130                       135                      140

Arg  Lys  Gln  Met  Ala  Val  Lys  Lys  Tyr  Leu  Ala  Ala  Val  Leu  Gly  Lys
145                       150                       155                     160

Arg  Tyr  Lys  Gln  Arg  Val  Lys  Asn  Lys  Gly  Arg  Arg  Ile  Ala  Tyr  Leu
               165                       170                      175
```

( 2 ) INFORMATION FOR SEQ ID NO:9:

( i ) SEQUENCE CHARACTERISTICS:
        ( A ) LENGTH: 44 amino acids
        ( B ) TYPE: amino acid
        ( D ) TOPOLOGY: linear ( i i ) MOLECULE TYPE: protein (x i) SEQUENCE DESCRIPTION: SEQ ID NO:9:

| Tyr | Ala | Asp | Ala | Ile | Phe | Thr | Asn | Ser | Tyr | Arg | Lys | Val | Leu | Gly | Gln |
| 1 | | | | 5 | | | | | 10 | | | | | | 15 |

| Leu | Ser | Ala | Arg | Lys | Leu | Leu | Gln | Asp | Ile | Met | Ser | Arg | Gln | Gln | Gly |
| | | | 20 | | | | | 25 | | | | | 30 | | |

| Glu | Ser | Asn | Gln | Glu | Arg | Gly | Ala | Arg | Ala | Arg | Leu |
| | | | 35 | | | | 40 | | | | |

(2) INFORMATION FOR SEQ ID NO:10:

(i) SEQUENCE CHARACTERISTICS:
      (A) LENGTH: 27 amino acids
      (B) TYPE: amino acid
      (D) TOPOLOGY: linear (i i) MOLECULE TYPE: protein (x i) SEQUENCE DESCRIPTION: SEQ ID NO:10:

| His | Ser | Asp | Gly | Thr | Phe | Thr | Ser | Glu | Leu | Ser | Arg | Leu | Arg | Glu | Gly |
| 1 | | | | 5 | | | | | 10 | | | | | | 15 |

| Ala | Arg | Leu | Gln | Arg | Leu | Leu | Gln | Gly | Leu | Val |
| | | | 20 | | | | | 25 | | |

(2) INFORMATION FOR SEQ ID NO:11:

(i) SEQUENCE CHARACTERISTICS:
      (A) LENGTH: 28 amino acids
      (B) TYPE: amino acid
      (D) TOPOLOGY: linear (i i) MOLECULE TYPE: protein (x i) SEQUENCE DESCRIPTION: SEQ ID NO:11:

| His | Ser | Asp | Ala | Val | Phe | Thr | Asp | Asn | Tyr | Thr | Arg | Leu | Arg | Lys | Gln |
| 1 | | | | 5 | | | | | 10 | | | | | | 15 |

| Met | Ala | Val | Lys | Lys | Tyr | Leu | Asn | Ser | Ile | Leu | Asn |
| | | | 20 | | | | | 25 | | | |